United States Patent [19]
Pfister et al.

[11] Patent Number: 5,688,795
[45] Date of Patent: Nov. 18, 1997

[54] [3-(4-PHENYLPIPERAZIN-1-YL)PROPYL-AMINO, THIO AND OXY]-PYRIDINE, PYRIMIDINE AND BENZENE DERIVATIVES AS $\alpha_1$-ADRENOCEPTOR ANTAGONISTS

[75] Inventors: Jürg Roland Pfister, Los Altos; David Ernest Clarke, Mountain View; Todd Richard Elworthy, Palo Alto; David John Morgans, Jr., Los Altos; David Bruce Repke, Milpitas; Eric Brian Sjorgren, Mountain View; Helen Yen-hui Wu, San Jose, all of Calif.

[73] Assignee: Syntex (U.S.A.) Inc., Palo Alto, Calif.

[21] Appl. No.: 336,368

[22] Filed: Nov. 8, 1994

[51] Int. Cl.$^6$ .............. A61K 31/495; C07D 401/12; C07D 403/12; C07D 413/14
[52] U.S. Cl. ............ 514/252; 514/235.8; 514/255; 544/121; 544/131; 544/295; 544/334; 544/357; 544/360; 544/364; 544/365; 544/369; 544/379; 544/392; 544/393; 546/316; 560/161
[58] Field of Search .............. 544/121, 295, 544/357, 360, 364, 365, 369, 392–394; 514/252, 255, 235.8

[56] References Cited

U.S. PATENT DOCUMENTS

| | | | |
|---|---|---|---|
| 4,060,526 | 11/1977 | Shetty | 544/393 |
| 4,616,017 | 10/1986 | Baldwin et al. | 514/252 |
| 5,164,397 | 11/1992 | George et al. | 514/275 |
| 5,244,894 | 9/1993 | George et al. | 514/252 |

FOREIGN PATENT DOCUMENTS

| | | |
|---|---|---|
| 2 567 885 | 1/1986 | France . |
| 21 39 083 | 2/1973 | Germany . |
| 2143730 | 3/1973 | Germany . |
| 49-133380 | 12/1974 | Japan . |

OTHER PUBLICATIONS

Klemm et al, *Chemical Abstracts*, vol. 78, No. 124625 (Abstract for DE 2139083, Feb. 15, 1973) (1973).
Marvyama et al, *Chemical Abstracts*, vol. 83, No. 43320 (Abstract for JP 74,133,380, Dec. 21, 1974) (1975).
S.K. Starling et al., "Anti-inflammatory and Anti-arrhythmic Activities of 1-(Alkanoylphenoxy/Thiophenoxy)-3-N$^4$-phenylpiperazinyl)propanes", *Ind. J. Chem.*, 15B(8), 715–719 (1977).
S.N. Rastogi et al., "Agents Acting on the Central Nervous System. 19. (±)-1-o -and m-Alkanoylphenoxy)-3(N$^4$-arylpiperazinyl)propan-2-ols as Local Anesthetics, Hypotensives, and Tranquillizers", *J. Med. Chem.*, 16(7), 797–804 (1973).
S.F. Campbell et al., "2,4-Diamino-6, 7-dimethoxyquinazolines. 1. 2-[4-(Benzodioxan-2-ylcarbonyl)-piperazin-1-yl]Derivatives as $\alpha_1$-Adrenoceptor Antagonists and Antihypertensive Agents", *J. Med. Chem.*, 30(1), 49–57 (1987);(and *Chem. Abs.*, 106(13), 102231a (1987) ).

H. Azuma et al., "$\alpha_1$-Adrenoceptor antagonist activity of novel pyrimidine derivatives (SHI437 and IK29) in rabbit aorta and trigone of the bladder", *Br. J. Pharmacol.*, 96(4), 1000–1006 (1989); (and *Chem. Abs.*, 111(3), 17522e (1989) ).

*Primary Examiner*—Emily Bernhardt
*Attorney, Agent, or Firm*—Heller Ehrman White & McAuliffe

[57] ABSTRACT

The present invention relates to novel $\alpha_1$-adrenoceptor antagonists of Formula I:

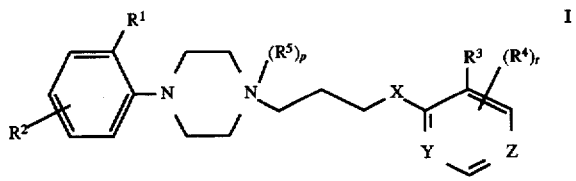

in which:

p is 0 or 1;

t is 0, 1 or 2;

X is O, S or NR$^6$ (in which R$^6$ is hydro or (C$_{1-6}$)alkyl);

Y and Z are independently CH or N;

R$^1$ is hydro, hydroxy, halo, nitro, amino, cyano, (C$_{1-4}$) alkylthio, acetylamino, trifluoroacetylamino, methylsulfonylamino, (C$_{1-6}$)alkyl, (C$_{3-6}$)cycloalkyl, (C$_{3-6}$)cycloalkyl (C$_{1-4}$)alkyl, oxazol-2-yl, aryl, heteroaryl, aryl (C$_{1-4}$)alkyl, heteroaryl (C$_{1-4}$)alkyl, (C$_{1-6}$)alkyloxy, (C$_{3-6}$)cycloalkyloxy, (C$_{3-6}$)cycloalkyl (C$_{1-4}$)alkyloxy, 2-propynyloxy, aryloxy, heteroaryloxy, aryl (C$_{1-4}$)alkyloxy or heteroaryl (C$_{1-4}$)alkyloxy (wherein alkyl is optionally substituted with one to three halo atoms and aryl or heteroaryl is optionally substituted with one to two substituents independently selected from halo and cyano);

R$^2$ is hydro, hydroxy, halo, cyano, (C$_{1-6}$)alkyl or (C$_{1-6}$) alkyloxy (wherein alkyl is optionally substituted with one to three halo atoms);

R$^3$ is -C (O)R$^7$ (wherein R$^7$ is (C$_{1-6}$)alkyl, (C$_{3-6}$) cycloalkyl, di(C$_{1-4}$)alkylamino, N-(C$_{1-4}$)alkyl-N-(C$_{1-4}$) alkyloxyamino, (C$_{1-4}$)alkyl((C$_{1-4}$)alkyloxy)amino, pyrrolidin-1-yl, piperidin-1-yl, morpholin-4-yl or piperazin-1-yl);

R$^4$ is halo, hydroxy, cyano, (C$_{1-6}$)alkyl or (C$_{1-6}$)alkyloxy; and

R$^5$ is (C$_{1-6}$)alkyl; and the pharmaceutically acceptable salts and N-oxides thereof.

19 Claims, No Drawings

[3-(4-PHENYLPIPERAZIN-1-YL)PROPYL-AMINO, THIO AND OXY]-PYRIDINE, PYRIMIDINE AND BENZENE DERIVATIVES AS $\alpha_1$-ADRENOCEPTOR ANTAGONISTS

FIELD OF THE INVENTION

This invention relates to novel [3-(4-phenylpiperazin-1-yl)propylamino]-pyridine, pyrimidine and benzene derivatives as $\alpha_1$-adrenoceptor antagonists, their uses as therapeutic agents, and the methods of their making.

BACKGROUND OF THE INVENTION $\alpha_1$-Adrenoceptor stimulation produces contraction of prostatic and lower urinary tract smooth muscle, leading to increased resistance in urinary outflow. Thus, $\alpha_1$-adrenoceptor antagonists are useful in treating conditions which relate directly or indirectly to obstructive uropathies, particularly obstruction due to benign prostatic hyperplasia (BPH) (Lepor, H. *The Prostate Supplement.* 1990, 3, 75–84). $\alpha_1$-Adrenoceptors also mediate the contractile state of vascular smooth muscle. Thus, $\alpha_1$-adrenoceptor antagonists find use as anti-hypertensive agents.

Most of the $\alpha_1$-adrenoceptor antagonists which have been or are currently prescribed for treating BPH were developed originally as antihypertensives. Those $\alpha_1$-adrenoceptor antagonists which were developed specifically for treating BPH also possess blood pressure lowering effects. Consequently, when these $\alpha_1$-adrenoceptor antagonist are used for treating BPH, hypotension and/or inhibition of the mechanism by which normal blood pressure is maintained during changes in posture (i.e., postural hypotension) are undesired side effects. Antagonists which can selectively reduce $\alpha_1$-adrenoceptor hyperactivity in prostatic and/or lower urinary tract smooth muscle, without affecting blood pressure or causing postural hypotension, are desirable.

The disclosures of these and other documents referred to throughout this application (e.g., in the Pharmacology section of the Detailed Description of the Invention) are incorporated herein by reference.

SUMMARY OF THE INVENTION

This application relates to a compound of Formula I:

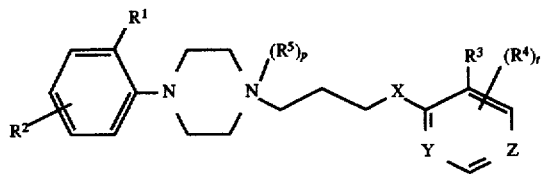

in which:
p is 0 or 1;
t is 0, 1 or 2;
X is O, S or $NR^6$ (in which $R^6$ is hydro or $(C_{1-6})$alkyl);
Y and Z are independently CH or N;
$R^1$ is hydro, hydroxy, halo, nitro, amino, cyano, $(C_{1-4})$alkylthio, acetylamino, trifluoroacetylamino, methylsulfonylamino, $(C_{1-6})$alkyl, $(C_{3-6})$cycloalkyl, $(C_{3-6})$cycloalkyl$(C_{1-4})$alkyl, oxazol-2-yl, aryl, heteroaryl, aryl$(C_{1-4})$alkyl, heteroaryl $(C_{1-4})$alkyl, $(C_{1-4})$alkyloxy, $(C_{3-6})$cycloalkyloxy, $(C_{3-6})$cycloalkyl $(C_{1-4})$alkyloxy, 2-propynyloxy, aryloxy, heteroaryloxy, aryl $(C_{1-4})$alkyloxy or heteroaryl $(C_{1-4})$alkyloxy (wherein alkyl is optionally substituted with one to three halo atoms and aryl or heteroaryl is optionally substituted with one to two substituents independently selected from halo and cyano);

$R^2$ is hydro, hydroxy, halo, cyano, $(C_{1-6})$alkyl or $(C_{1-6})$alkyloxy (wherein alkyl is optionally substituted with one to three halo atoms);

$R^3$ is $-C(O)R^7$ (wherein $R^7$ is $(C_{1-6})$alkyl, $(C_{3-6})$cycloalkyl di$(C_{1-4})$alkylamino, N—$(C_{1-4})$alkyl-N—$(C_{1-4})$alkyloxyamino, $(C_{1-4})$alkyl$((C_{1-4})$alkyloxy)amino, pyrrolidin-1-yl, piperidin-1-yl, morpholin-4-yl or piperazin-1-yl);

$R^4$ is halo, hydroxy, cyano, $(C_{1-6})$alkyl or $(C_{1-6})$alkyloxy; and $R^5$ is $(C_{1-6})$alkyl; and the pharmaceutically acceptable salts and N-oxides thereof.

A second aspect of this invention is a pharmaceutical composition which contains a compound of Formula I in admixture with one or more suitable excipients.

A third aspect of this invention is a method for treating a disease involving directly or indirectly an obstruction of the lower urinary tract in an animal in need of such treatment, particularly for treating obstruction due to benign prostate hyperplasia, which method comprises administering to such animal a therapeutically effective amount of a compound of Formula I or a pharmaceutically acceptable salt or salts or N-oxide thereof.

A fourth aspect of this invention is a method for preparing compounds of Formula I and is set forth in "Detailed Description of the Invention".

DETAILED DESCRIPTION OF THE INVENTION

Definitions:

Unless otherwise stated, the following terms used in the specification and claims have the meanings given below:

"Alkyl", as in $(C_{1-4})$alkylthio, $(C_{1-6})$alkyl or $(C_{1-6})$ alkyloxy, means a straight or branched saturated hydrocarbon radical having from one to the number of carbon atoms designated optionally substituted with one to three halo atoms (e.g., optionally substituted $(C_{1-4})$alkylthio includes methylthio, ethylthio, 2,2,2-trifluoroethylthio, etc.; optionally substituted $(C_{1-6})$alkyl includes methyl, trifluoromethyl, ethyl, propyl, isopropyl, butyl, isobutyl, sec-butyl, tert-butyl, etc.; and optionally substituted $(C_{1-6})$alkyloxy includes methoxy, difluoromethoxy, trifluoromethoxy, ethoxy, 2,2,2-trifluoroethoxy, propoxy, isopropoxy, butoxy, isobutoxy, sec-butoxy, tert-butoxy, etc.).

"Cycloalkyl", as in $(C_{3-6})$cycloalkyl, $(C_{3-6})$cycloalkyl$(C_{1-4})$alkyl, $(C_{3-6})$cycloalkyloxy or $(C_{3-6})$ cycloalkyl$(C_{1-4})$alkyloxy, means a saturated monocyclic hydrocarbon radical having from three to the number of carbon atoms designated (e.g., $(C_{3-6})$cycloalkyl includes the radicals cyclopropyl, cyclobutyl, cyclopentyl and cyclohexyl; and $(C_{3-6})$cycloalkyloxy includes the radicals cyclopropyloxy, cyclobutyloxy, cyclopentyloxy and cyclohexyloxy).

"Aryl", as in aryl, aryl$(C_{1-4})$alkyl, aryloxy and aryl$(C_{1-4})$ alkyloxy, means an organic radical derived from an aromatic hydrocarbon containing 6 to 14 carbon atoms and includes monocyclic or condensed carbocyclic aromatic rings (e.g., phenyl, naphthyl, anthracenyl, phenanthrenyl, etc.) optionally substituted with one to two substituents independently selected from halo and cyano.

"Heteroaryl", as in heteroaryl, heteroaryl $(C_{1-4})$alkyl, heteroaryloxy and heteroaryl $(C_{1-4})$alkyloxy, means an organic radical derived from an aromatic hydrocarbon containing 5 to 14 atoms, 1 to 5 of which are hereto atoms chosen from N, O, or S, and includes monocyclic, condensed heterocyclic and condensed carbocyclic and heterocyclic aromatic rings (e.g., thienyl, furyl, pyrrolyl, pyrimidinyl, isoxazolyl, indolyl, benzo[b]thienyl, isobenzofuranyl, purinyl, isoquinolyl, pterdinyl, perimidinyl, imidazolyl, pyridyl, pyrazolyl, pyrazinyl, etc.) optionally substituted with one two substituents independently selected from halo and cyano.

"Halo" means fluoro, chloro, bromo, or iodo.

"Leaving group" has the meaning conventionally associated with it in synthetic organic chemistry, i.e., an atom or group displaceable under alkylating conditions, and includes halogen and alkane- or arenesulfonyloxy, such as mesyloxy, ethanesulfonyloxy, benzenesulfonyloxy and tosyloxy, and thienyloxy, dihalophosphinoyloxy, tetrahalophosphaoxy, and the like.

"Animal" includes humans, non-human mammals, e.g., dogs, cats, rabbits, cattle, horses, sheep, goats, swine, and deer, and non-mammals, e.g., birds and the like.

"Disease" specifically includes any unhealthy condition of an animal or part thereof and includes an unhealthy condition which may be caused by, or incident to, medical or veterinary therapy applied to that animal, i.e., the "side effects" of such therapy.

"Optional" or "optionally" means that the subsequently described event or circumstance may or may not occur, and that the description includes instances where the event or circumstance occurs and instances in which it does not. For example, the phrase "wherein alkyl is optionally substituted with one to three halo atoms and aryl or heteroaryl is optionally substituted with one to two substituents independently selected from halo and cyano" means that the alkyl, aryl and heteroaryl radicals referred to may or may not be substituted in order to fall within the scope of the invention.

"Protective group" has the meaning conventionally associated with it in synthetic organic chemistry, i.e., a group which selectively blocks one reactive site in a multifunctional compound such that a chemical reaction can be carried out selectively at another unprotected reactive site and which can be readily removed after the selective reaction is completed.

"Protective agent" means an agent which will react with a multifunctional compound and create a protective group at reactive nitrogen atoms.

"Protected" in reference to a compound or a group means a derivative of compound or group in which a reactive site or sites are blocked with protective groups.

"Deprotecting" refers to removing any protective groups present after the selective reaction has been carried out.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrobromic acid, hydrochloric acid, nitric acid, phosphoric acid, sulfuric acid and the like; or with organic acids such as acetic acid, benzenesulfonic acid, benzoic acid, camphorsulfonic acid, p-chlorobenzene-sulfonic acid, cinnamic acid, citric acid, cyclopentanepropionic acid, 1,2- ethanedisulfonic acid, ethanesulfonic acid, fumaric acid, glucoheptonic acid, gluconic acid, glutamic acid, glycolic acid, hexanoic acid, heptanoic acid, o-(4-hydroxybenzoyl) benzoic acid, 2-hydroxyethanesulfonic acid, hydroxynaphthoic acid, lactic acid, lauryl sulfuric acid, maleic acid, malic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-naphthalenesulfonic acid, oxalic acid, 3-phenylpropionic acid, propionic acid, pyruvic acid, salicylic acid, stearic acid, succinic acid, tartaric acid, tertiary butylacetic acid, p-toluenesulfonic acid, trimethylacetic acid and the like.

Pharmaceutically acceptable salts also include base addition salts which may be formed when acidic protons present are capable of reacting with inorganic or organic bases. Acceptable inorganic bases include aluminum hydroxide, calcium hydroxide, potassium hydroxide, sodium carbonate and sodium hydroxide. Acceptable organic bases include diethanolamine, ethanolamine, N-methylglucamine, triethanolamine, tromethamine and the like.

"N-Oxide", when referring to a compound of Formula I, means such compound in which Y and/or Z is N in an oxidized state, i.e., O←N. The N-oxides of compounds of Formula I can be prepared by methods known to those of ordinary skill in the art.

"Therapeutically effective amount" means that amount which, when administered to an animal for treating a disease, is sufficient to effect such treatment for the disease.

The term "q.s." means adding a quantity sufficient to achieve a stated function, e.g., to bring a solution to the desired volume (i.e., 100%).

"Treating" or "treatment" of a disease includes:

(1) preventing the disease from occurring in an animal which may be predisposed to the disease but does not yet experience or display symptoms of the disease, (2) inhibiting the disease, i.e., arresting its development, or (3) relieving the disease, i.e., causing regression of the disease.

The compounds of Formula I are named in accordance with acceptable nomenclature rules generally consistent with "Chemical Abstracts"; however, for the purpose of consistency some deviation from the general rule may occur. For example, the compound of Formula I in which t is 0, X is NH, $R^1$ is methoxy and $R^2$ and $R^5$ are each hydro, i.e., a compound of the following formula:

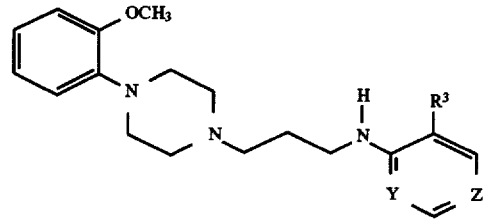

is named N,N-diethyl-2-{3-[4-(2-methoxyphenyl) piperazin-1-yl]propylamino}nicotinamide when Y is N, Z is CH and $R^3$ is diethylaminocarbonyl;

is named N,N-diethyl-4-{3-[4-(2-methoxyphenyl) piperazin-1-yl]propylamino}nicotinamide when Y is CH, Z is N and $R^3$ is diethylaminocarbonyl;

is named N,N-diethyl-2-{3-[4-(2-methoxyphenyl) piperazin-1-yl]propylamino}benzamide when Y and Z are each CH and $R^3$ is diethylaminocarbonyl; is named N,N-diethyl-2-{3-[4-(2-methoxyphenyl)piperazin-1-yl]propylamino}pyrimidine-5-carboxamide when Y and Z are each N and $R^3$ is diethylaminocarbonyl;

is named 2-{3-[4-(2-methoxyphenyl)piperazin-1-yl]propylamino}-N-pyrrolidin-1-ylnicotinamide when Y is N, Z is CH and $R^3$ is pyrrolidin-1-ylcarbonyl; and is named 2-{3-[4-(2-methoxyphenyl)piperazin-1-yl]propylamino}-N-morpholin-4-ylnicotinamide when Y is N, Z is CH and $R^3$ is morpholin-4-ylcarbonyl.

Presently Preferred Embodiments:

While the broadest definition of this invention is set forth in the Summary of the Invention, certain compounds of Formula I are preferred. For example, preferred compounds of Formula I are those in which p is 0, t is 0 or 1, X is NH, Y is CH or N, Z is CH, $R^1$ is methylthio, methylsulfonylamino, $(C_{1-4})$alkyl, cyclopropyl, oxazol-2-yl, $(C_{1-3})$alkyloxy, cyclopropylmethoxy (wherein alkyl in any of the above is optionally substituted with three halo groups); $R^2$ is hydro, fluoro or methyl; $R^3$ is dimethylaminocarbonyl or N-methyl-N-methoxyaminocarbonyl; and $R^4$ is a substitution at the 5-position selected from halo, cyano or methyl.

Particularly preferred compounds of Formula I are those in which p is 0, t is 0, X is NH, Y is N, Z is CH, $R^1$ is methylthio, n-propyl, cyclopropyl, oxazol-2-yl, methoxy, trifluoromethoxy, 2,2,2-trifluoroethoxy or cyclopropylmethoxy; $R^2$ is hydro, fluoro or methyl; and $R^3$ is dimethylaminocarbonyl or N-methyl-N-methoxyaminocarbonyl.

Pharmacology and Utility:

The $\alpha_1$-adrenoceptor pharmacology of the compounds of this invention was determined by art-recognized procedures. In vitro assays for measuring the relative effect of test compounds on $\alpha_1$-adrenoceptor mediated contraction of rat isolated aortic and rabbit isolated urinary bladder smooth muscle are described in Example 39. In vitro assays for measuring the relative effect of test compounds on $\alpha_1$-adrenoceptor mediated contraction of human isolated arterial, prostatic and urinary bladder smooth muscle are described in Example 40. An in vivo assay for measuring the blood pressure lowering effects of test compounds in normotensive and spontaneously hypertensive rats is described in Example 41. An in vivo assay for measuring the effect of test compounds on the reflex maintenance of basal blood pressure in response to postural change from supine to vertical is described in Example 42. An in vivo assay for measuring the relative effect of test compounds on $\alpha_1$-adrenoceptor mediated increases in blood and intraurethral pressures is described in Example 43.

In summary, the compounds of this invention were tested by the procedures described above and found to selectively inhibit the $\alpha_1$-adrenoceptors which mediate the contractile state of prostatic and lower urinary tract smooth muscle. The compounds of this invention will decrease resistance in urinary outflow, without producing the blood pressure lowering effects and/or the postural hypotension that are associated with previously described $\alpha_1$-adrenoceptor antagonists. Accordingly, the compounds of this invention are useful in treating conditions which relate directly or indirectly to obstructive uropathies, particularly obstruction due to benign prostatic hyperplasia.

Administration and Pharmaceutical Composition:

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from 0.1 micrograms per kilogram body weight (µg/kg) per day to 1 milligram per kilogram body weight (mg/kg) per day, typically 1 µg/kg/day to 10 µg/kg/day. Therefore, a therapeutically effective amount for a 80 kg human may range from 8 µg/day to 800 mg/day, typically 80 µg/day to 0.8 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of Formula I will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the confound of Formula I in aerosol form. Inert gases suitable for this purpose are nitrogen, carbon dioxide, nitrous oxide, etc. Other suitable pharmaceutical carriers and their formulations are described in A. R. Alfonso *Remington's Pharmaceutical Sciences* 1985, 17th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise from 0.000001% w to 10.0% w of the compound of Formula I, preferably 0.00001% w to 1.0% w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 38.

Processes for Preparing Compounds of the Invention:

Compounds of Formula I in which p is 0 and one or both of Y and Z are N can be prepared by the process depicted by the following Reaction Scheme I:

Scheme I

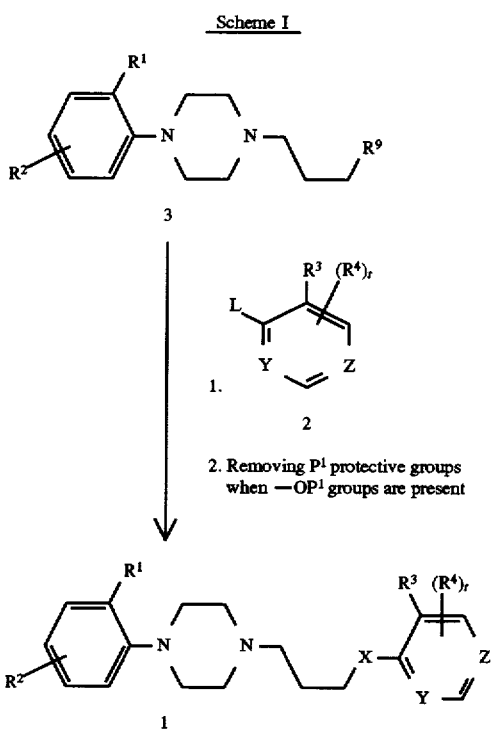

in which $R^9$ is hydroxy, mercapto or —$NHR^6$ and each t, X, Y, Z, $R^1$, $R^2$, $R^3$, $R^4$ and $R^6$ are as defined in the Summary of the Invention with respect to Formula I (with the proviso that one or both of Y and Z are N and any hydroxy groups present in compounds of Formulae 2 and 3 are protected by a $P^1$ protective group).

Compounds of Formula I in which p is 0 and one or both of Y and Z are N (Formula 1) can be prepared by reacting a compound of Formula 2 with a compound of Formula 3 and then removing $P^1$ protective groups when any protected hydroxy groups are present. The reaction between the compounds of Formulae 2 and 3 is carried out preferably in the presence of a suitable base, typically a nitrogen base (e.g., triethylamine, N,N-diisopropylethylamine, etc.) or a carbonate salt base (e.g., potassium carbonate, sodium carbonate, cesium carbonate, etc.) and preferably potassium carbonate, in a suitable inert organic solvent (e.g., xylene, toluene, N,N-dimethylformamide (DMF), N-methylpyrrolidine, N-methylpyrrolidinone (NMP), dimethylsulfoxide (DMSO), 1,3-dimethyl-3,4,5,6-tetrahydro-2 (1H)-pyrimidinone (DMPU), any appropriate mixture of suitable solvents, etc.), preferably a nonpolar aprotic solvent (e.g, xylene, toluene, benzene, etc.) and most preferably xylene, at 80° to 180° C., typically at 100° to 140° C. and preferably at reflux temperature, and requires 4 to 48 hours.

Each hydroxy group present in the compound of Formula 2 or 3 should be protected with a suitable $P^1$ protective group (e.g., benzyl, para-methoxybenzyl, 1-naphthylmethyl, etc., preferably benzyl). After the selective reaction between the compounds of Formulae 2 and 3 is carried out the $P^1$ protective groups are removed. Removal of the $P^1$ protective group is carried out by any means which gives the desired unprotected product in reasonable yield. A detailed description of the techniques applicable to protective groups and their removal can be found in T. W. Greene, *Protective Groups in Organic Synthesis*, John Wiley & Sons, Inc. 1981. For example, a convenient method of removing a benzyl protective group is by catalytic hydrogenation. The hydrogenation is carried out with a suitable catalyst (e.g., 10% palladium on carbon (10% Pd/C), palladium hydroxide, palladium acetate, etc. preferably 10% Pd/C) in the presence of ammonium formate and in an appropriate solvent, typically an alcohol (e.g., ethanol, methanol, isopropanol, any appropriate mixture of alcohols, etc., preferably methanol) at 50° to 66° C., typically at 63° to 66° C. and preferably at approximately reflux temperature. Alternatively, the hydrogenation is carried out with hydrogen gas at 0 to 50 psi, typically at 10 to 20 psi and preferably at approximately 15 psi, at 20° to 50° C., typically at 23° to 27° C. and preferably at 23° C. The preparation of a compound of Formula I in which one or both of Y and Z are N is described in Example 21.

Compounds of Formula 3 in which $R^9$ is amino (hereinafter designated as compounds of Formula 3(a)) can be prepared by reacting an optionally substituted 4-phenylpiperazine of Formula 5:

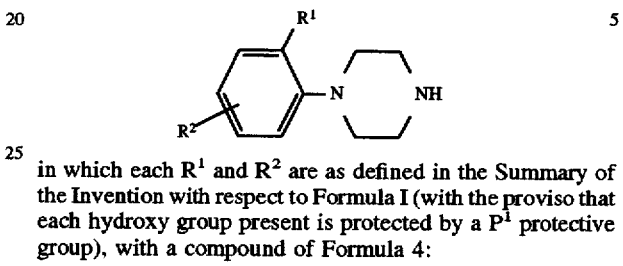

in which each $R^1$ and $R^2$ are as defined in the Summary of the Invention with respect to Formula I (with the proviso that each hydroxy group present is protected by a $P^1$ protective group), with a compound of Formula 4:

Br⁀⁀⁀⁀$R^8$  4 in which $R^8$ is —$NHP^2$ (wherein $P^2$ is a protective group) or phthalimido and then deprotecting. The reaction between the compounds of Formulae 4 and 5 is carried out in the presence of a suitable base, typically a nitrogen or a carbonate salt base and preferably potassium carbonate, in a suitable inert organic solvent (e.g., DMF, acetonitrile, NMP, any appropriate mixture of suitable solvents, etc., preferably DMF) at 20° to 100° C., typically at 40° to 80° C. and preferably at approximately 80° C., and requires 1 to 8 hours. The deprotection is effected by any means which gives the desired product in reasonable yield. Hydroxy groups present in the compound of Formula 5 should be protected with a suitable protective group. When protected hydroxy groups are present, the removal of the $p^2$ protective group must be effected by a means that which will not remove the $P^1$ protective groups.

A convenient method of deprotecting when $P^2$ is benzyloxycarbonyl is by catalytic hydrogenation. The hydrogenation is carried out with a suitable catalyst (e.g., 10% Pd/C, palladium hydroxide, palladium acetate, etc., preferably 10% Pd/C) at 20° to 80° C., typically at 20° to 40° C. and preferably at below 30° C., and 0 to 100 psi, typically at 15 to 50 psi and preferably at approximately 35 psi, and requires 2 to 24 hours. A convenient method of deprotecting when $R^8$ is phthalimido can be effected by hydrazinolyzsis, which is carried out by reacting with hydrazine in a suitable solvent, typically an alcohol (e.g., ethanol, methanol, isopropanol, any appropriate mixture of alcohols, etc., preferably ethanol), at 20° to 100° C., typically at 50° to 80° C. and preferably at approximately reflux temperature, and requires 2 to 24 hours.

Alternatively, compounds of Formula 3(a) can be prepared by (i) reacting a compound of Formula 5 with acrylamide to give a 3-(4-phenylpiperazin-1-yl)propionamide of Formula 6:

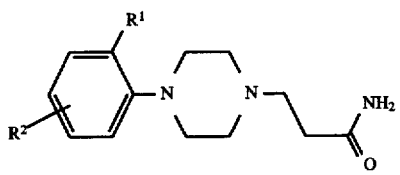

6 in which each $R^1$ and $R^2$ are as defined in the Summary of the Invention with respect to Formula I (with the proviso that each hydroxy group present is protected by a $P^1$ protective group) and (ii) reducing the compound of Formula 6 to give the compound of Formula 3(a). The reaction between the compound of Formula 5 and the acrylamide is carried out in a suitable solvent, typically water, an alcohol or an amide (e.g., water, methanol, ethanol, DMF, any appropriate mixture of suitable solvents, etc., preferably water), at 20° to 100° C., typically at 40° to 80° C. and preferably at approximately 80° C., and requires 1 to 6 hours. The reduction of the propionamide can be effected with a suitable chemical reducing agent (e.g., borane-tetrahydrofuran complex, borane.dimethyl sulfide, lithium aluminum hydride, sodium borohydride with boron trifluoride etherate, etc., preferably borane.tetrahydrofuran complex) in a suitable solvent (e.g., tetrahydrofuran (THF), tert-butylmethyl ether, ethylene glycol dimethyl ether (DME), toluene, any appropriate mixture of suitable solvents, etc., preferably THF) at 60° to 110° C., typically at 60° to 80° C. and preferably at reflux temperature, requiring 4 to 10 hours.

Typically, compounds of Formula 3 in which $R^9$ is —$NHR^6$, wherein $R^6$ is ($C_{1-6}$)alkyl, are prepared by reacting a compound of Formula 5 with a compound of Formula 4 in which $R^8$ is —$NHP^2$, alkylating and then deprotecting. The alkylation is carried out with an appropriate alkylating agent (e.g., iodomethane, allyl bromide, n-hexyliodide, etc.) in the presence of a strong base (e.g., sodium hydride, potassium hydride, lithium hexamethyldisilazide, etc., preferably sodium hydride) and in a suitable solvent (e.g., DMF, THF, ethylene glycol, any appropriate mixture of suitable solvents, etc., preferably DMF) at 0° to 50° C., typically at 10° to 25° C. and preferably at approximately 20° C., and requires 1 to 65 hours. Preparations of compounds of Formula 3 in which $R^9$ is —$NHR^6$ (hereinafter designated as compounds of Formula 3(b)) are described in Examples 7, 8, 9 and 11.

Compounds of Formula 3 in which $R^9$ is hydroxy (hereinafter designated as compounds of Formula 3(c)) can be prepared by reacting a compound of Formula 5 with 3-bromo-1-propanol in the presence of a suitable base, typically a nitrogen base or a carbonate salt base and preferably potassium carbonate, and optionally in the presence of an iodide salt (e.g., sodium iodide, lithium iodide, tetraalkylammonium iodides such as tetramethyammonium iodide and the like, etc., preferably sodium iodide)in a suitable inert organic solvent (e.g., acetonitrile, DMF, NMP, DMSO, toluene, any appropriate mixture of suitable solvents, etc., preferably acetonitrile) at 80° to 160° C., typically at 80° to 90° C. and preferably at reflux temperature, requiring 1 to 8 hours. The preparation of a compound of Formula 3(c) is described in Example 10.

Typically, compounds of Formula 3 in which $R^9$ is mercapto (hereinafter designated as compounds of Formula 3(d)) are prepared by converting a compound of Formula 3(c) to a compound of Formula 7:

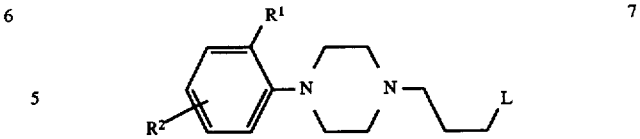

7 in which L is a leaving group and each $R^1$ and $R^2$ are as defined in the Summary of the Invention with respect to Formula I (with the proviso that each hydroxy group present is protected by a $P^1$ protective group), reacting the compound of Formula 7 with thioester salt (e.g., potassium thioacetate, potassium thiobenzoate, etc., preferably potassium thioacetate) and then de-alkanoylating. De-alkanoylating refers to removing the alkanoyl protective group after the reaction with the thioester salt is complete (e.g., removing the acetyl or benzoyl group when the thioester salt is thioacetate of thiobenzoate, respectively). For example, the preparation of a compound of Formula 3(d) is carried out readily by reacting the compound of Formula 7 with potassium thioacetate in a suitable solvent (e.g., methylene chloride, chloroform, 1,2-dichloroethane, nitromethane, DMF, any appropriate mixture of solvents, etc., preferably DMF) at 20° to 80° C., typically at 40° to 60° C. and preferably at approximately 50° C., for 12 to 50 hours and then de-acetylating with an appropriate chemical reducing agent (e.g., sodium borohydride, lithium aluminum hydride, lithium borohydride, etc.) in a suitable alcohol solvent (e.g., 2-ethoxyethanol, ethanol, isopropanol, methanol, any appropriate mixture of suitable alcohols, etc., preferably methanol,) at 0° to 50° C., typically at 20° to 25° C. and preferably at approximately 25° C., requiring 1 to 24 hours. Alternatively, the de-alkanoylation can be effected with an aqueous base 0° to 50° C., typically at 0° to 30° C. and preferably at approximately 25° C., requiring 1 to 24 hours.

The conversion of a compound of Formula 3(c) to a compound of Formula 7 is effected by treating with an appropriate agent for forming a suitable leaving group (e.g., methanesulfonyl chloride, p-toluene sulfonylchloride, thionyl chloride, phosphorous pentachloride, phosphorous oxychloride, and the like). For example, a compound of Formula 7 in which L is mesyloxy can be prepared by treating a compound of Formula 3(c) with methanesulfonyl chloride in a suitable inert organic solvent (e.g., methylene chloride, dichloroethane, pyridine, etc., preferably methylene chloride) at 0° to 25° C., typically at 0° to 10° C. and preferably at approximately 0° C., requiring 0.5 to 2 hours. The preparation of a compound of Formula 3(d) is described in Example 12.

Compounds of Formula 5 can be prepared by reacting optionally substituted aniline with bis(chloroethyl)amine hydrochloride. The reaction is carried out preferably in the presence of a suitable base, typically a nitrogen base or a carbonate salt base and preferably potassium carbonate, and optionally in the presence of an iodide salt (e.g., sodium iodide, lithium iodide, tetraalkylammonium iodides such as tetramethyammonium iodide and the like, etc., preferably sodium iodide), and in a suitable solvent, typically an alcohol or ether (e.g., n-butanol, tert-butanol, 2-methoxyethyl ether (diglyme), any appropriate mixture of suitable solvents, etc., preferably n-butanol), at 50° to 160° C., typically at 80° to 160° C. and preferably at reflux temperature, and requires 2 to 24 hours. Optionally substituted anilines are commercially available or can be prepared by methods known to those of ordinary skill in the art.

Compounds of Formula 5 can be prepared from optionally substituted N-(2-anilino)ethyl-2-oxazolidinone. The preparation is carried out by stirring the oxazolidone with excess molar equivalents of acid, typically 1 to 20 molar equivalents of acid and preferably approximately 15 molar equivalents of hydrobromic acid, in a suitable solvent, typically an aqueous acid or water (e.g., acetic acid, propionic acid, water, any appropriate mixture of suitable solvents, etc., preferably acetic acid), at 20° to 80° C., typically at 20° to 40° C. and preferably at approximately 20° C., to give the corresponding N-2-bromoethyl-N'-phenyl-1,2-ethanediamine dihydrobromide and then cyclizing by heating in a suitable solvent, typically an alcohol (e.g., ethanol, methanol, isopropanol, any appropriate mixture of suitable alcohols, etc., preferably ethanol) under an inert atmosphere (e.g., argon, nitrogen, etc.) at 50° to 85° C., typically at 78° to 85° C. and preferably at approximately reflux temperature, for 10 to 40 hours.

Protecting a compound of Formula 5 in which hydroxy groups are present can be effected by reacting the unprotected compound with a suitable protecting agent (e.g., benzyl bromide, benzyl chloride, 4-methoxybenzyl chloride, 1-bromomethylnaphthalene, etc., preferably benzyl bromide). For example, a compound of Formula 5 wherein $P^1$ is benzyl can be prepared by reacting an hydroxy substituted 1-tert-butoxycarbonyl-4-phenylpiperazine with benzyl bromide and then removing the tert-butoxycarbonyl group. The reaction with the benzyl bromide is carried out preferably in the presence of a suitable base, typically a nitrogen base or a carbonate salt base and preferably cesium carbonate, in a suitable inert organic solvent (e.g., DMF, NMP, THF, DME, any appropriate mixture of suitable solvents, etc., preferably DMF), under an inert atmosphere (e.g., nitrogen, argon, etc.) at 0° to 40° C., typically at 0° to 40° C. and preferably at approximately 25° C., and requires 1 to 24 hours. The tert-butoxycarbonyl group is removed readily with acid, (e.g., hydrochloric acid, trifluoroacetic acid, etc.) in a suitable solvent (e.g., methylene chloride, chloroform, 1,2-dichloroethane, any appropriate mixture of suitable solvents, etc., preferably methylene chloride) at 0° to 40° C., typically at 0° to 40° C. and preferably at approximately 25° C., requiring 1 to 10 hours. Preparations of compounds of Formula 5 are described in Examples 1, 2, 3, 4 and 5.

Compounds of Formula 4 in which $R^8$ is —$NP^2H$ can be prepared by reacting unprotected 3-bromopropylamine with 1 to 1.3 molar equivalents of a suitable amino group protecting agent (e.g., benzyl chloroformate, tert-butyl chloroformate, di-tert-butyl dicarbonate, etc., preferably benzyl chloroformate) in the presence of a suitable base, typically a nitrogen base or a carbonate salt base and preferably potassium carbonate. For example, a compound of Formula 4 wherein $P^2$ is benzyloxycarbonyl is prepared by reacting the unprotected amine with benzyl chloroformate in the presence of potassium carbonate in a suitable inert organic solvent, typically an aromatic hydrocarbon, or a mixture thereof in water, or halogenated hydrocarbon (e.g., toluene, 5/1 to 1/5 toluene/water, methylene chloride, chloroform, any appropriate mixture of suitable solvents, etc., preferably approximately 1/2 toluene/water), at 0° to 40° C., typically at 5° to 10° C. and preferably at approximately 5° C. The compound of Formula 4 is which $R^8$ is phthalimido is commercially available.

Compounds of Formula 2 in which L is chloro and $R^3$ is —$C(O)R^7$ wherein $R^7$ is $di(C_{1-4})$alkylamino, N—$(C_{1-6})$alkyl-N—$(C_{1-6})$alkyloxyamino, pyrrolidin-1-yl, piperidin-1-yl, morpholin-4-yl or piperazin-1-yl can be prepared by reacting a corresponding acid chloride with an appropriate amine (e.g., $di(C_{1-4})$alkylamine, N,O-dimethylhydroxylamine hydrochloride, pyrrolidine, etc.). The reaction is carried out in a suitable solvent, typically an ether or halogenated hydrocarbon (e.g., THF, diethyl ether, methylenechloride, dichloroethane, any appropriate mixture of suitable solvents, etc., preferably THF), at 0° to 50° C., typically at 0° to 25° C. and preferably at approximately 0° C., and requires 0.5 to 2 hours.

Acid chlorides which are useful in the preparation of compounds of Formula 2 are typically prepared by reacting an appropriate acid (e.g., 2-chloronicotinic acid, 4-chloronicotinic acid, 4-chloropyridazine-5-carboxylic acid, 4-hydroxypyridazine-5-carboxylic acid, etc.) with a suitable chlorinating agent (e.g., oxalyl chloride, thionyl chloride, phosphoric trichloride, etc, preferably oxalyl chloride), optionally in the presence of 0.01 to 0.05% DMF or like solvent. The reaction is carried out in a suitable solvent, typically an aromatic hydrocarbon or halogenated hydrocarbon (e.g., methylene chloride, 1,2-dichloroethane, toluene, any appropriate mixture of suitable solvents, etc., preferably methylene chloride), at 20° to 120° C., typically at 40° to 100° C. and preferably at approximately reflux temperature, and requires 1 to 8 hours.

Compounds of Formula 2 in which L is chloro and $R^3$ is —$C(O)R^7$ wherein $R^7$ is $(C_{1-6})$alkyl or $(C_{3-6})$cycloalkyl can be prepared by reacting a corresponding 2-chloronicotinic acid chloride with an appropriate lithium organocuprate such as lithium $di(C_{1-6})$alkylcuprate or $di(C_{3-6})$cycloalkylcuprate. The reaction is carried out in a suitable inert organic solvent (e.g., THF, diethyl ether, methylene chloride, 1,2-dimethoxyethane (glyme), any appropriate mixture of suitable solvents, etc., preferably THF) at −78° to 0° C., typically at −30° to −40° C. and preferably at approximately −40° C., and requires 0.5 to 2 hours. The lithium organocuprate is formed by reacting copper halide, preferably copper(I) iodide, with 2 molar equivalents of an appropriate organolithium compound at −78° to 0° C., typically at −40° to −30° C. and preferably at approximately −40° C., requiring 0.5 to 2 hours.

Compounds of Formula 2 in which $R^3$ is —$C(O)R^7$ wherein $R^7$ is $(C_{1-6})$alkyl or $(C_{3-6})$cycloalkyl can be prepared readily by reacting a corresponding 2-chloronicotinic acid chloride with an appropriate organotin compound. The reaction can be carried out in the presence of a suitable palladium catalyst (e.g., bis(benzonitrile)palladium(II) chloride, tetrakis(triphenylphosphine)palladium(0), etc., preferably bis(benzonitrile)palladium(II) chloride) in a suitable aprotic solvent (e.g., hexamethylphosphoramide (HMPA), NMP, DMF, any appropriate mixture of suitable solvents, etc., preferably HMPA) at 20° to 80° C., typically at 20° to 40° C. and preferably at approximately 20° C., requiring 2 to 24 hours. Alternatively, the reaction with the organotin compound is carried out in the presence of n-butyllithium and copper(I) iodide in a suitable solvent, typically an ether or methoxy substituted hydrocarbon (e.g., THF, diethyl ether, glyme, any appropriate mixture of suitable solvents, etc., preferably THF) at −78° to 0° C., typically at −30° to −40° C. and preferably at approximately −40° C., requiring 0.5 to 2 hours. Preparations of compounds of Formula 2 are described in Examples 13, 14, 15, 16, 17, 18, 19 and 20.

Compounds of Formula I in which both Y and Z are CH can be prepared by reacting a compound of Formula 7 with a compound of Formula 8:

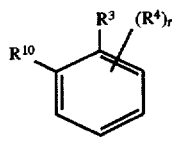

in which $R^{10}$ hydroxy, mercapto, —$NHR^6$ or —$NH^3$ (in which $P^3$ is a protective group) and each t, $R^3$ and $R^4$ are as defined in the Summary of the Invention with respect to Formula I (with the proviso that each $R^4$ that is hydroxy is protected by a $P^1$ protective group), and then removing any $P^1$ and $P^3$ protective groups that are present. When $R^{me}$ is hydroxy, mercapto or —$NHR^6$, the reaction is carried out preferably in the presence of a suitable base, typically a nitrogen base or a carbonate salt base and preferably cesium or potassium carbonate, and optionally in the presence of an iodide salt (e.g., sodium iodide, lithium iodide, tetraalkylammonium iodides such as tetramethyammonium iodide and the like, etc., preferably sodium iodide) and in a suitable inert organic solvent (e.g., acetonitrile, DMF, NMP, DMSO, any appropriate mixture of solvents, etc., preferably acetonitrile) at 80° to 140° C., typically at 80° to 110° C. and preferably at approximately 100° C., and requires 8 to 48 hours.

When R is —$NHP^3$, the reaction is carried out in the presence of a strong base (e.g., sodium hydride, potassium hydride, lithium hexamethyldisilazide, etc., preferably sodium hydride) in a suitable solvent (e.g., DMF, THF, ethylene glycol, any appropriate mixture of solvents, etc., preferably DMF) at 20° to 100° C., typically at 50° to 80° C. and preferably at approximately 80° C., and requires 1 to 30 hours. Suitable protective groups include trifluoroacetyl, benzene sulfonyl, acetyl, tert-butyloxycarbonyl, etc., preferably trifluoroacetyl. The protective group is normally cleaved under the given reaction conditions. When necessary the protective group can be removed by treating with a mild base (e.g., potassium carbonate, sodium carbonate, cesium carbonate, etc.) in a suitable solvent, typically an aqueous alcohol or any appropriate mixture of suitable alcohols and preferably aqueous methanol, at 30° to 40° C., typically at 0° to 40° C. and preferably at approximately 25° C., requiring 1 to 24 hours.

Compounds of Formula 8 in which $R^{10}$ is amino and $R^3$ is —$C(O)R^7$ wherein $R^7$ is di($C_{1-4}$)alkylamino, pyrrolidin-1-yl, piperidin-1-yl, morpholin-4-yl or piperazin-1-yl can be prepared by reacting an optionally substituted 2-nitrobenzoic acid chloride with an appropriate amine (e.g., di($C_{1-4}$)alkylamine, pyrrolidine, etc.) to give the corresponding 2-nitrobenzamide, which is then hydrogenated. The reaction with the amine is carried out in a suitable inert organic solvent (e.g., dioxane, THF, pyridine, methylene chloride, any appropriate mixture of suitable solvents, etc., preferably dioxane) at 0° to 25° C., typically at 10° to 25° C. and preferably at approximately 20° C., and requires 0.5 to 2 hours. The hydrogenation is carried out with a suitable catalyst (e.g., 5% palladium on carbon (5% Pd/C), palladium hydroxide, palladium acetate, etc., preferably 5% Pd/C) at 20° C. to 50° C., typically at 20° to 40° C. and preferably at approximately 25° C., and 15 to 50 psi, typically at 15 to 30 psi and preferably at approximately 15 psi, and requires 4 to 24 hours.

The 2-nitrobenzoic acid chloride is prepared by reacting the corresponding 2-nitrobenzoic acid with a suitable chlorinating agent (e.g., oxalyl chloride, thionyl chloride, phosphoric trichloride, etc, preferably oxalyl chloride), optionally in the presence of 0.1 to 0.5% DMF or like solvent. The reaction is carried out in a suitable solvent, typically a halogenated hydrocarbon or ester (e.g., methylene chloride, dichloroethane, ethyl acetate, any appropriate mixture of suitable solvents, etc., preferably methylene chloride), under an inert atmosphere (e.g., nitrogen, argon, etc.) at 15° to 20° C., typically at 20° to 40° C. and preferably at approximately 20° C., requiring 1 to 8 hours.

Proceeding similarly, compounds of Formula 8 in which $R^{10}$ is hydroxy and $R^3$ is —$C(O)R^7$ wherein $R^7$ is di($C_{1-4}$) alkylamino, pyrrolidin-1-yl, piperidin-1-yl, morpholin-4-yl or piperazin-1-yl can be prepared by reacting optionally substituted acetylsalicyloyl chloride with an appropriate amine to give the corresponding 2-acetoxybenzamide and then de-acetylating. The de-acetylation can be effected with a suitable base (e.g., sodium hydroxide, potassium hydroxide, etc.) at 0° to 50° C., typically at 20° to 30° C. and preferably at approximately 25° C., and requires 1 to 48 hours.

Proceeding similarly, compounds of Formula 8 in which $R^m$ is mercapto and $R^3$ is —$C(O)R^7$ wherein $R^7$ is di($C_{1-4}$) alkylamino, pyrrolidin-1-yl, piperidin-1-yl, morpholin-4-yl or piperazin-1-yl can be prepared by reacting 2,2'-dithiosalicyclic acid chloride with an appropriate amine to give the corresponding 2,2'-dithiosalicyclic acid amide, which is then reduced. The reduction can be effected with sodium borohydride at 0° to 40° C., typically at 0° to 30° C. and preferably at approximately 25° C., and requires 1 to 24 hours.

Compounds of Formula 8 in which $R^{10}$ is amino and $R^3$ is —$C(O)R^7$ wherein $R^7$ is ($C_{1-4}$)alkyl or ($C_{3-6}$)cycloalkyl can be prepared by reacting a corresponding 2-nitrobenzoic acid chloride with an appropriate lithium organocuprate such as lithium di($C_{1-4}$)alkylcuprate or di($C_{3-6}$) cycloalkylcuprate to give the corresponding 2-nitrophenyl ketone and then hydrogenating. The reaction with the organocuprate is carried out in a suitable solvent, typically an ether (e.g., THF, diethyl ether, ethylene glycol dimethyl ether, tert-butyl methyl ether, any appropriate mixture of suitable solvents, etc., preferably THF), at −90° to 0° C., typically at −40° to −30° C. and preferably at approximately −40° C., and requires 0.2 to 2 hours. The hydrogenation is carried out as described above for that of the 2-nitrobenzamide.

Proceeding similarly, compounds of Formula 8 in which $R^{10}$ is hydroxy and $R^3$ is —$C(O)R^7$ wherein $R^7$ is ($C_{1-4}$) alkyl or ($C_{3-6}$)cycloalkyl can be prepared by reacting a corresponding acetylsalicyloyl chloride with an appropriate lithium organocuprate to give the corresponding 2-acetoxyphenyl ketone and then de-acetylating as described above for the de-acetylation of the 2-acetoxybenzamide. Proceeding similarly, compounds of Formula 8 in which $R^{10}$ is mercapto and $R^3$ is —$C(O)R^7$ wherein $R^7$ is ($C_{1-4}$)alkyl or ($C_{3-6}$)cycloalkyl can be prepared by reacting a corresponding 2,2'-dithiosalicyclic acid with an appropriate lithium organocuprate to give the corresponding 2,2'-dithiophenyl ketone and then reducing as described above for reduction of the 2,2'-dithiosalicyclic acid amide.

Compounds of Formula 8 in which $R^{10}$ is —$NHR^6$ can be prepared by reacting a compound of Formula 8 in which $R^{10}$ is amino with an appropriate alkylating agent in the presence of a suitable base. Compounds of Formula 8 in which $R^{10}$ is —$NHP^3$ are prepared by treating a corresponding compound of Formula 8 in which $R^{10}$ is amino with 1 to 1.5 molar equivalents of a suitable amino group protecting agent (e.g., trifluoroacetic anhydride, benzene sulfonyl chloride, acetic anhydride, etc., preferably trifluoroacetic anhydride). For example, a compound of Formula 8 in which $P^3$ is trifluoroacetyl is prepared by treating the unprotected amine with trifluoroacetic anhydride in the presence of a suitable base (e.g., pyridine, triethylamine, diisopropylethylamine, etc., preferably pyridine) at −10° to 25° C., typically at 0° to 20° C., requiring 1 to 14 hours. Preparations of compounds of Formula 8 are described in Examples 22, 23, 24 and 25.

Compounds of Formula I in which both Y and Z are CH can be prepared by reacting a compound of Formula 8 with 3-bromo-1-propanol to give a compound of Formula 10:

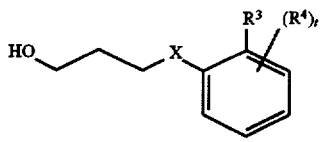

in which each X, t, $R^3$ and $R^4$ are as defined in the Summary of the Invention with respect to Formula I (with the proviso that each $R^4$ that is hydroxy is protected by a $P^1$ protective group), converting the compound of Formula 10 to a compound of Formula 9:

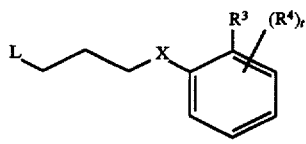

in which L is a leaving group, reacting the compound of Formula 9 with a compound of Formula 5, and then removing any $P^1$ and $P^3$ protective groups that are present.

The reaction between the compounds of Formulae 5 and 9 is carried out preferably in the presence of a suitable base, typically a nitrogen base or a carbonate salt base and preferably potassium carbonate, and optionally in the presence of an iodide salt (e.g., sodium iodide, lithium iodide, tetraalkylammonium iodides such as tetramethyammonium iodide and the like, etc., preferably sodium iodide) and in a suitable inert organic solvent (e.g., acetonitrile, DMF, NMP, DMSO, any appropriate mixture of suitable solvents, etc., preferably acetonitrile) at 80° to 140° C., typically at 80° to 110° C. and preferably at approximately 100° C., and requires 8 to 48 hours.

The conversion of the compound of Formula 10 to the compound of Formula 9 can be carried out with an appropriate agent for forming a suitable leaving group (e.g., methanesulfonyl chloride, p-toluene sulfonylchloride, thionyl chloride, phosphorous pentachloride, phosphorous oxychloride, and the like). The reaction between the compounds of Formula 8 and the 3-bromo-1-propanol is carried out in a suitable inert organic solvent (e.g., acetonitrile, DMF, NMP, DMSO, toluene, any appropriate mixture of suitable solvents, etc., preferably acetonitrile) at 80° to 160° C., typically at 100° to 140° C. and preferably at reflux temperature, and requires 1 to 8 hours. The preparation of a compound of Formula 9 is described in Example 28. Preparations of compounds of Formula I in which both Y and Z are CH are described in Examples 26, 27 and 29.

Additional Processes

Compounds of Formula I in which $R^1$ is amino can be prepared by hydrogenating a compound of Formula I in which $R^1$ is nitro. The hydrogenation is carried out with a suitable catalyst (e.g., 10% Pd/C, palladium hydroxide, palladium acetate, etc., preferably 10% Pd/C) in a suitable alcohol solvent (e.g., ethanol, methanol, any appropriate mixture of suitable alcohols, etc., preferably ethanol) at 20° to 40° C., typically at 20° to 30° C. and preferably at approximately 25° C., and 15 to 40 psi, typically at 15 to 30 psi and preferably at approximately 15 psi, and requires 4 to 24 hours. The preparation of a compound of Formula I in which $R^1$ is amino is described in Example 36.

Compounds of Formula I in which $R^1$ is acetylamino, trifluoroacetylamino or methylsulfonylamino can be prepared by reacting a compound of Formula I in which $R^1$ is amino with acetic anhydride, trifluoroacetic anhydride or methanesulfonyl chloride, respectively. The reaction is carried out in a suitable inert organic solvent (e.g., pyridine, 2,6-dimethylpyridine, dichloromethane, triethylamine, any appropriate mixture of suitable solvents, etc., preferably pyridine) at 0° to 40° C., typically at 0° to 10° C. and preferably at approximately 0° C., and requires 0.5 to 3 hours. The preparation of a compound of Formula I in which $R^1$ is methylsulfonylamino is described in Example 37.

Compounds of Formula I in which $R^5$ is $(C_{1-6})$alkyl and $R^6$ is hydro can be prepared by reacting a corresponding compound of Formula I in which p is 0 with an appropriate alkylating agent in a suitable inert organic solvent (e.g., ethanol, acetonitrile, DMF, NMP, any appropriate mixture of suitable solvents, etc., preferably ethanol). The reaction is carried out at 0° to 30° C., typically at 20° to 30° C. and preferably at approximately 20° C., and requires 12 to 72 hours. The preparation of a compound of Formula I in which $R^5$ is methyl is described in Example 30.

Compounds of Formula I in which $R^6$ is $(C_{1-6})$alkyl can be prepared by reacting a compound of Formula I in which $R^6$ is hydro with an appropriate alkylating agent. The alkylation is carried out in the presence of a strong base (e.g., sodium hydride, potassium hydride, lithium hexamethyldisilazide, etc., preferably sodium hydride) and in a suitable inert organic solvent (e.g., DMF, THF, ethylene glycol dimethyl ether, any appropriate mixture of suitable solvents, etc., preferably DMF) at 0° to 50° C., typically at 10° to 25° C. and preferably at approximately 20° C., and requires 1 to 65 hours. Compounds of Formula I in which $R^5$ and $R^6$ are each $(C_{1-6})$alkyl can be prepared by proceeding as described above but carrying out the alkylation at 20° to 80° C., typically at 50° to 70° C. and preferably at approximately 50° C., requiring 5 to 24 hours. The preparation of a compound of Formula I in which $R^5$ and $R^6$ are each methyl is described in Example 31.

Compounds of Formula I in which $R^1$ and/or $R^2$ is hydroxy can be prepared by demethylating a compound of Formula I in which $R^1$ and/or $R^2$ is methoxy. The demethylation is carried out by standard methods with an appropriate demethylating agent (e.g., sodium cyanide, boron tribromide, boron trichloride, etc., preferably sodium cyanide) in a suitable inert organic solvent (e.g., DMSO, NMP, HMPA, methylene chloride, 1,2-dichloroethane, any appropriate mixture of suitable solvents, etc., preferably DMSO) at 80° to 180° C., typically at 100° to 160° C. and preferably at reflux temperature, and requires 2 to 24 hours. The preparation of a compound of Formula I in which $R^1$ is hydroxy is described in Example 32.

Compounds of Formula I in which one or both of Y and Z are N and $R^4$ is halo can be prepared by halogenating a compound of Formula I in which one or both of Y and Z are N and t is 0. The halogenation can be carried out with a suitable halogenating agent (e.g., N-chlorosuccinimide (NCS), N-bromosuccinimide (NBS), etc.) in the presence of 1 equivalent of acid (e.g., hydrochloric acid, hydrobromic acid, etc.) and in a suitable inert organic solvent (e.g., DMF, DMSO, DMPU, NMP, any appropriate mixture of suitable solvents, any appropriate mixture of suitable solvents, etc., preferably DMF) at 0° to 100° C., typically at 20° to 60° C. and preferably at approximately 55° C., requiring 1 to 12 hours. The preparation of a compound of Formula I in which $R^4$ is chloro is described in Example 33.

Compounds of Formula I in which R² is halo can be prepared by halogenating a compound of Formula I in which R² is hydro. The halogenation can be carried out with a suitable halogenating agent (e.g., NCS, NBS, etc.) in the presence of at least 6 equivalents of acid (e.g., hydrochloric acid, hydrobromic acid, etc.) and in a suitable inert organic solvent (e.g., DMF, DMSO, DMPU, NMP, any appropriate mixture of suitable solvents, etc., preferably DMF) at 0° to 100° C., typically at 20° to 60° C. and preferably at approximately 20° C., requiring 1 to 12 hours. The preparation of a compound of Formula I in which R² is bromo is described in Example 34.

Compounds of Formula I in which R² or R⁴ is cyano can be prepared by cyano-de-halogenation of a compound of Formula I in which R² or R⁴ is halo. The reaction is carried out with copper(I) cyanide in a suitable inert organic solvent (e.g., NMP, DMPU, DMF, any appropriate mixture of suitable solvents, etc., preferably NMP) under an inert atmosphere (e.g., argon, nitrogen, etc.) at 150° to 220° C., preferably at approximately 200° C., and requires 8 to 24 hours. The preparation of a compound of Formula I in which R² is cyano is described in Example 35.

Compounds of Formula I may be prepared as pharmaceutically acceptable acid addition salts by reacting the free base forms of a compound of Formula I with a pharmaceutically acceptable inorganic or organic acid. Alternatively, the pharmaceutically acceptable base addition salts of compounds of Formula I may be prepared by reacting the free acid forms of compounds of Formula I with pharmaceutically acceptable inorganic or organic bases. Inorganic and organic acids and bases suitable for the preparation of the pharmaceutically acceptable salts of compounds of Formula I are set forth in the definitions section of this application. Alternatively, the salt forms of the compounds of Formula I may be prepared using salts of the starting materials or intermediates.

The free acid or free base forms of the compounds of Formula I can be prepared from the corresponding base addition salt or acid addition salt form. For example, compounds of Formula I in an acid addition salt form may be converted to the corresponding free base by treating with a suitable base (e.g., ammonium hydroxide solution, sodium hydroxide, etc.). Compounds of Formula I in a base addition salt form may be converted to the corresponding free acid by treating with a suitable acid (e.g., hydrochloric acid, etc).

The N-oxides of the compounds of Formula I can be prepared by treating an unoxidized form of the compound of Formula I with an oxidizing agent (e.g., trifluoroperacetic acid, permaleic acid, perbenzoic acid, peracetic acid, metachloroperoxybenzoic acid, etc.) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material, i.e., by proceeding as in Reaction Scheme I with the N-oxide of a compound of Formula 2.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, etc.) in an suitable inert organic solvent (e.g., acetonitrile, ethanol, aqueous dioxane, etc.) at 0° to 80° C.

In summary, an aspect of this invention is a process for preparing a compound of Formula I:

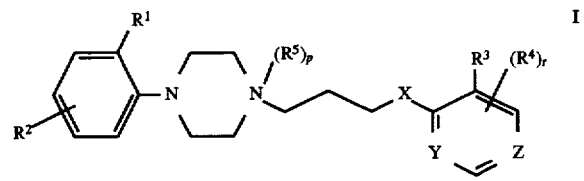

in which:

p is 0 or 1;

t is 0, or 2;

X is O, S or NR⁶ (in which R⁶ is hydro or $(C_{1-6})$alkyl);

Y and Z are independently CH or N;

R¹ is hydro, hydroxy, halo, nitro, amino, cyano, $(C_{1-4})$ alkylthio, acetylamino, trifluoroacetylamino, methylsulfonylamino, $(C_{1-6})$alkyl, $(C_{3-6})$cycloalkyl, $(C_{3-6})$cycloalkyl$(C_{1-4})$alkyl, oxazol-2-yl, aryl, heteroaryl, aryl $(C_{1-4})$ alkyl, heteroaryl $(C_{1-4})$alkyl, $(C_{1-6})$alkyloxy, $(C_{3-6})$cycloalkyloxy, $(C_{3-6})$cycloalkyl $(C_{1-4})$alkyloxy, 2-propynyloxy, aryloxy, heteroaryloxy, aryl $(C_{1-4})$alkyloxy or heteroaryl$(C_{1-4})$alkyloxy (wherein alkyl is optionally substituted with one to three halo atoms and aryl or heteroaryl is optionally substituted with one to two substituents independently selected from halo and cyano);

R² is hydro, hydroxy, halo, cyano, $(C_{1-6})$alkyl or $(C_{1-6})$ alkyloxy (wherein alkyl is optionally substituted with one to three halo atoms);

R³ is –C(O)R⁷ (wherein R⁷ is $(C_{1-6})$alkyl, $(C_{3-6})$ cycloalkyl, di$(C_{1-4})$alkylamino, N-$(C_{1-4})$alkyl-N-$(C_{1-4})$ alkyloxyamino, $(C_{1-4})$alkyl($(C_{1-4})$alkyloxy)amino, pyrrolidin-1-yl, piperidin-1-yl, morpholin-4-yl or piperazin-1-yl );

R⁴ is halo, hydroxy, cyano, $(C_{1-6})$alkyl or $(C_{1-6})$alkyloxy; and

R⁵ is $(C_{1-6})$alkyl; and the pharmaceutically acceptable salts and N-oxides thereof, which process comprises:

(A) wherein p is 0 and one or both of Y and Z are N, (i) reacting a compound of Formula 3:

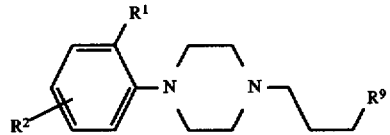

in which R⁹ is hydroxy, mercapto or –NHR⁶ and each R¹, R² and R⁶ are as defined above (with the proviso that each R¹ and/or R² that is hydroxy is protected by a P¹ protective group) with a compound of Formula 2:

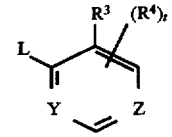

in which t, Y, Z, R³ and R⁴ are as above (with the proviso that one or both of Y and Z are N and each hydroxy group present is protected by a P¹ protective group), and then removing any P¹ protective groups that are present;

(B) wherein Y and Z are each CH, (i) converting a compound of Formula 3 in which R⁹ is hydroxy to a compound of Formula 7:

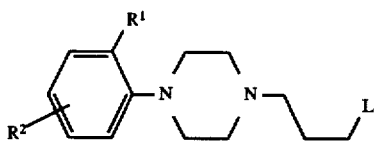

in which L is a leaving group and each $R^1$ and $R^2$ are as defined above (with the proviso that each hydroxy group present is protected by a $P^1$ protective group); and (ii) reacting the compound of Formula 7 with a compound of Formula 8:

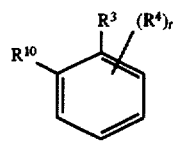

in which $R^{10}$ is hydroxy, mercapto, $-NHR^6$ or $-NHP^3$ (wherein $P^3$ is a protective group) and each t, $R^3$ and $R^4$ are as defined above (with the proviso that each $R^4$ group that is hydroxy is protected by a $P^1$ protective group), and then removing any $P^1$ and $P^3$ protective groups that are present;

(C) wherein Y and Z are each CH, (i) reacting a compound of Formula 8 with 3-bromo-1-propanol to give a compound of Formula 10:

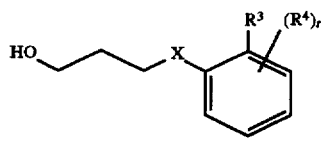

in which each X, t, $R^3$ and $R^4$ are as defined above (with the proviso that each $R^4$ that is hydroxy is protected by a $P^1$ protective group);

(ii) converting the compound of Formula 10 to give a compound of Formula 9:

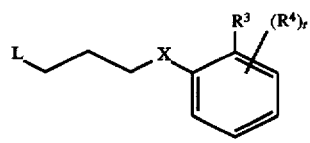

in which L is a leaving group;

(iii) reacting the compound of Formula 9 with a compound of Formula 5:

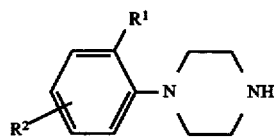

in which each $R^1$ and $R^2$ are as defined above (with the proviso that each hydroxy group present is protected by a $P^1$ protective group) and removing any $p^1$ and $p^3$ protective groups that are present;

(D) optionally halogenating a compound of Formula I in which $R^2$ is hydro to give a compound of Formula I in which $R^2$ is halo;

(E) optionally halogenating a compound of Formula I in which one or both of Y and Z are N and t is 0 to give a compound of Formula I in which one or both of Y and Z are N and $R^4$ is halo;

(F) optionally demethylating a compound of Formula I in which $R^1$ is methoxy to give a compound of Formula I in which $R^1$ is hydroxy;

(G) optionally cyano-de-halogenating a compound of Formula I in which $R^2$ or $R^4$ is halogen to give a compound of Formula I in which $R^2$ of $R^4$, respectively, is cyano;

(H) optionally reducing a compound of Formula I in which $R^1$ is nitro to give a compound of Formula I in which $R^1$ is amino;

(I) optionally reacting a compound of Formula I in which $R^1$ is amino with acetic anhydride, trifluoroacetic anhydride or methanesulfonyl chloride to give a compound of Formula I in which $R^1$ is acetylamino, trifluoroacetylamino or methylsulfonylamino, respectively;

(J) optionally alkylating a compound of Formula I in which p is 0 to give a compound of Formula I in which $R^5$ is $(C_{1-6})$alkyl;

(K) optionally alkylating a compound of Formula I in which $R^6$ is hydro to give a compound of Formula I in which $R^6$ is $(C_{1-6})$alkyl;

(L) optionally oxidizing a compound of Formula I to give an N-oxide derivative thereof;

(M) optionally reducing an N-oxide derivative of a compound of Formula I to unoxidized form;

(N) optionally converting a compound of Formula I into a pharmaceutically acceptable salt; and (O) optionally converting a salt form of a compound of Formula I to non-salt form.

EXAMPLE 1

1-[2-(Difluoromethoxy)phenyl]piperazine

The following is the preparation of a compound of Formula 5 in which $R^1$ is difluoromethoxy and $R^2$ is hydro.

A mixture of 2-nitrophenol (6.01 g, 43.2 mmol) and sodium hydroxide (8.6 g, 216 mmol) in 50 mL of dioxane and 50 mL of water was heated to 70° C. and chlorodifluoromethane gas was introduced. The mixture was diluted with water and extracted with diethyl ether. The organic phase was washed with aqueous sodium hydroxide and then brine, dried (MgSO$_4$) and concentrated to give 1-difluoromethoxy-2-nitrobenzene (8.21 g, 43.4 mmol) as an oil.

A mixture of 1-difluoromethoxy-2-nitrobenzene (8.21 g, 43.4 mmol) and 10% palladium on carbon (1.1 g) in 100 mL of ethanol was stirred under a hydrogen atmosphere at room temperature for approximately 24 hours. The mixture was filtered and the filtrate was concentrated to give 2-difluoromethoxyaniline (5.14 g, 32.3 mol) as an oil.

A mixture of 2-difluoromethoxyaniline (5.14 g, 32.3 mmol) and bis(chloroethyl)amine hydrochloride (5.8 g, 32.5 mmol) in 50 mL of n-butanol was heated at reflux for 48 hours. Potassium carbonate (8.9 g, 64.5 mmol) was added and heated at reflux for approximately 24 hours. The mixture was extracted with 2N hydrochloric acid and the extract cooled to approximately 0° C. and then basified with sodium hydroxide to give a precipitate. The precipitate was extracted with ethyl acetate. The ethyl acetate extract was washed with brine, dried (MgSO$_4$) and concentrated. The residue was purified by column chromatography eluting with 5% methanol/methylene chloride. Product fractions were combined and concentrated. The residue was crystallized from hydrochloric acid in methanol to give 1-[2-(difluoromethoxy)phenyl]piperazine hydrochloride (1.32 g, 4.38 mmol), m.p. 165°–176° C.

EXAMPLE 2

1-[2-(2,2,2-Trifluoroethoxy)phenyl]piperazine

The following is the preparation of a compound of Formula 5 in which $R^1$ is 2,2,2-trifluoroethoxy and $R^2$ is hydro.

A mixture of 2-(2,2,2-trifluoroethoxy)aniline (3.89 g, 20.4 mmol), bis(2-chloroethyl)amine hydrochloride (3.64 g, 20.4 mmol), potassium carbonate (2.82 g, 20.4 mmol) and sodium iodide (0.6 g, 4.1 mmol) in 10 mL of 2-methoxyethyl ether was heated at reflux for 4.5 hours. The mixture was cooled and 20 mL of an aqueous solution at pH 9 was added. The mixture was extracted with ethyl acetate (4×50 mL) and the combined organic layers were washed with brine, dried ($Na_2SO_4$) and concentrated. The residue was purified on silica gel by column chromatography eluting with 5% methanol/methylene chloride to give 1-[2-(2,2,2-trifluoroethoxy)phenyl]piperazine (2.74 g, 10.6 mmol). The free base was recrystallized from hydrochloric acid in alcohol to give 1-[2-(2,2,2-trifluoroethoxy)phenyl]piperazine hydrochloride, m.p. 172°–173° C.

Proceeding as in Example 2 but substituting different starting materials for 2-(2,2,2-trifluoroethoxy)aniline the following compounds of Formula 5 were prepared:

substituting 2-trifluoromethylaniline gave 1-(2-trifluoromethylphenyl)-piperazine;

substituting 2-trifluoromethoxyaniline gave 1-(2-trifluoromethoxyphenyl)-piperazine;

substituting 2-n-propylaniline gave 1-(2-n-propylphenyl) piperazine, m.p. 213°–215° C.;

substituting 2-neopentoxyaniline gave 1-(2-neopentoxyphenyl)piperazine;

substituting 2-(2-propynyloxy)aniline gave 1-[2-(2-propynyloxy)phenyl]-piperazine;

substituting 2-cyclopropylaniline gave 1-(2-cyclopropylphenyl)piperazine dihydrochloride, m.p. 124°–133° C.;

substituting 2-benzylaniline gave 1-(2-benzylphenyl) piperazine; substituting N-(2-aminophenyl)acetamide gave N-(2-piperazin-1-ylphenyl)acetamide;

substituting N-(2-aminophenyl)trifluoroacetamide gave N-(2-piperazin-1-yl-phenyl)trifluoroacetamide;

substituting 4-methyl-2-methoxyaniline gave 1-(4-methyl-2-methoxyphenyl)-piperazine, m.p. 207°–224° C.;

substituting 5-chloro-2-methoxyaniline gave 1-(5-chloro-2-methoxyphenyl)-piperazine;

substituting 4-fluoro-2-methoxyaniline gave 1-(4-fluoro-2-methoxyphenyl)-piperazine dihydrochloride, m.p. 202°–204° C.;

substituting 5-fluoro-2-methoxyaniline gave 1-(5-fluoro-2-methoxyphenyl)-piperazine, dihydrochloride, m.p. 181°–184° C.;

substituting 2-bromo-4-fluoroaniline gave 1-(2-bromo-4-fluorophenyl)piperazine;

substituting 2,4-di(2,2,2-trifluoroethoxy)aniline gave 1-[2,4-di(2,2,2-trifluoroethoxy)phenyl]piperazine;

substituting 2-aminobiphenyl gave 1-biphen-2-ylpiperazine; and substituting 2-(2,2,2-trifluoroethoxy)-2-methylaniline gave 1-[2-(2,2,2-trifluoroethoxy)-4-methylphenyl] piperazine.

EXAMPLE 3

1-(2-Oxazol-2-ylphenyl)piperazine

The following is the preparation of a compound of Formula 5 in which $R^1$ is oxazol-2-yl and $R^2$ is hydro.

A mixture of 2-fluorobenzoic acid (4.5 g, 32.14 mmol) and oxalyl chloride (4.1 mL, 48.2 mL) in 2 drops of DMF and 40 mL of methylene chloride was heated at reflux for 2 hours. The mixture was allowed to cool to room temperature and stirred for approximately 12 hours and then the solvents were removed by rotary evaporation. The residue was slowly added to a suspension of 2-bromoethylamine hydrobromide (5.7 g, 28 mmol) and triethylamine (21 mL, 160 mmol) in 200 mL of benzene. The mixture was heated at reflux for 12 hours, allowed to cool to room temperature and then stirred for an additional 12 hours. The mixture was quenched with water and the aqueous layer was separated and extracted with methylene chloride (2×50 mL). The combined extracts were dried ($MgSO_4$) and concentrated. The residue was purified on silica gel by column chromatography eluting with hexanes/ethyl acetate (5:1) to give 2-fluoro-1-(4,5-dihydrooxazol-2-yl)benzene (1.96 g, 11.9 mmol).

A mixture of 2-fluoro-1-(4,5-dihydrooxazol-2-yl)benzene (4.5 g, 27.3 mmol) and nickel peroxide hydrate (7 g) in 40 mL of benzene was heated at reflux for 24 hours. The mixture was allowed to cool to room temperature, filtered and concentrated by rotary evaporation. The residue was purified on silica gel by column chromatography eluting with hexanes/ethyl acetate (5:1) to give 2-fluoro-1-oxazol-2-yl-benzene (0.5 g, 3.07 mmol).

A solution of N-benzylpiperazine (3.56 g, 20.2 mmol) in 25 mL of THF was cooled to 0° C. and then n-butyllithium was added. The mixture was stirred at 0° C. for 30 minutes and at room temperature for an additional hour. The mixture was cooled to 0° C. and then 2-fluoro-1-oxazol-2-ylbenzene (1.1 g, 6.75 mmol) was slowly added. The mixture was allowed to warm to room temperature and stirred at room temperature for 90 minutes. The mixture was quenched with water and the aqueous layer was separated and extracted with ethyl acetate (3×30 mL). The combined extract was washed with brine, dried ($MgSO_4$) and concentrated. The residue was purified on silica gel by column chromatography eluting with hexanes/ethyl acetate (10:1) to give 4-benzyl-1-(2-oxazol-2-ylphenyl)piperazine (0.805 g, 2.52 mmol).

A mixture of 4-benzyl-1-(2-oxazol-2-ylphenyl)piperazine (0.906 g, 2.84 mmol) and 10% palladium on carbon (1 g) in 20 mL of methanol was stirred under a hydrogen atmosphere (1 atm) at room temperature for 4 hours. The mixture was filtered and concentrated by rotary evaporation to give 1-(2-oxazol-2-ylphenyl)piperazine (0.480 g, 2.1 mmol).

EXAMPLE 4

1-(4-Benzyloxy-2-methoxyphenyl)piperazine

The following is the preparation of a compound of Formula 5 in which $R^1$ is methoxy and $R^2$ is benzyloxy.

A mixture of 1-(2,4-dimethoxyphenyl) piperazine hydrochloride (3.1 g, 13.9 mmol) in 30 mL of approximately 40% aqueous hydrogen bromide was heated at reflux for 30 hours and then the volatiles were removed in vacuo. Recrystallization of the residue from methanol gave 1-(4-hydroxy-2-methoxyphenyl)piperazine dihydrobromide (4.6 g, 12.4 mmol), m.p. >280° C.

1-(4-Hydroxy-2-methoxyphenyl)piperazine dihydrobromide (1.95 g, 5.27 mmol) was dissolved in 10 mL of THF and 10 mL of saturated sodium bicarbonate solution and then di(tert-butyl)pyrocarbonate (1.35 g, 6.2 mmol) was added. The mixture was stirred vigorously at room temperature for 18 hours and extracted with diethyl ether (3×25 mL). The combined extracts were washed with brine, dried ($MgSO_4$) and filtered. The solvents were removed in vacuo and the residue was dissolved in 20 mL of DMF. The solution was treated with cesium carbonate (1.46 g, 4.5 mmol) and then benzyl bromide (1.1 g, 4.6 mmol) and stirred at room temperature under nitrogen for 3 hours. The mixture was partitioned between 50 mL of water and 50 mL of diethyl ether. The aqueous layer was separated and extracted with diethyl ether (2×50 mL). The combined diethyl ether was washed with brine, dried (MgSO$_4$), filtered and concentrated. The residue was purified on silica gel by column chromatography eluting with hexanes/ethyl acetate (3:1) to give a pale yellow oil. The oil was dissolved in 20 mL of methylene chloride and the solution was treated with 10 mL of trifluoroacetic acid. After 45 minutes at room temperature the mixture was partitioned between 100 mL of 5M aqueous potassium carbonate and 100 mL of methylene chloride. The aqueous layer was separated and extracted with methylene chloride (2×100 mL). The combined methylene chloride was washed with brine, dried (Na$_2$SO$_4$), filtered and concentrated to give 1-(4-benzyloxy-2-methoxyphenyl)piperazine (1.39 g, 4.7 mmol).

EXAMPLE 5

1-(2-isopropylphenyl)piperazine

The following is the preparation of a compound of Formula 5 in which $R^1$ is isopropyl and $R^2$ is hydro.

A mixture of N-[2-(2-isopropylanilino)ethyl]-2-oxazolindinone (1.4 g, 5.6 mmol) in 30% hydrobromic acid in acetic acid was stirred at room temperature for 25 hours. The mixture was diluted with 80 mL of methylene chloride and stirred for 0.5 hours. The mixture was filtered and the filtered solids were dissolved in 20 mL of ethanol. The solution was heated at 50° to 60° C. under nitrogen for approximately 65 hours and at reflux under nitrogen for approximately 90 hours. The solution was allowed to cool to room temperature and then the solvent was removed under reduced pressure by rotary evaporation to give 1-(2-isopropylphenyl)piperazine hydrobromide (1.167 g, 4.09 mmol), m.p. 240°–241° C.

EXAMPLE 6

Benzyl (3-bromopropyl)aminoformate

The following is the preparation of a compound of Formula 4 in which the protective group is benzyloxycarbonyl.

A solution of 3-bromopropylamine hydrobromide (547.5 g, 2.5 mol) in 500 mL of toluene and 600 mL of water was cooled to 6° C. and then aqueous potassium carbonate (1L, 5M, 5 mol) and benzyl chloroformate (1L, 2.63 mol) were added simultaneously at a rate such that the reaction temperature remained below 16° C. The mixture was allowed to warm to room temperature and then stirred for 80 minutes and 1.3L of additional water was added. The aqueous later was separated and extracted with toluene (1×300 mL). The combined organic layers were washed with 1N hydrochloric acid (2×300 mL), saturated sodium bicarbonate (1×300 mL) and saturated aqueous sodium chloride (1×300 mL), dried (Na$_2$SO$_4$) and filtered. The filtrate was concentrated under reduced pressure and the residue was extracted with hexanes (3×1L). The extract was concentrated under reduced pressure at 50° C. to give benzyl (3-bromopropyl)aminoformate (612.9 g, 2.25 mol) as a liquid.

EXAMPLE 7

3-[4-(2-Methoxyphenyl)piperazin-1-yl]propylamine

The following is the preparation of a compound of Formula 3 in which $R^1$ is methoxy, $R^2$ is hydro and $R^9$ is amino.

A mixture of benzyl (3-bromopropyl)aminoformate (495.2 g, 1.82 mol), prepared as in Example 6, 1-(2-methoxyphenyl)piperazine hydrochloride (377.9 g, 1.65 mol) and potassium carbonate (456.8 g, 3.31 mol) in 3L of DMF was stirred at 80° to 81° C. for 3.5 hours. The mixture was allowed to cool to room temperature and then poured into 20L of water. The mixture was extracted with ethyl acetate (3×4L). The combined ethyl acetate extracts were washed with water (2×1L) and saturated aqueous sodium chloride (1×1L), dried (Na$_2$SO$_4$) and treated with silica gel (200 g). The ethyl acetate was filtered and 11L of the filtrate was added slowly to 200 mL of 5.5N hydrochloric acid (2.75 mol) in ethanol at a rate such that the reaction temperature did not exceed 23° C. The mixture was aged at room temperature for 1 hour and filtered. The filtered residue was washed with ethyl acetate (3×500 mL), dried under a stream of air for 17 hours and then dried under reduced pressure at 60° C. to give benzyl 3-[4-(2-methoxyphenyl)piperazin-1-yl]propylaminoformate dihydrochloride (496 g, 1.09 mol), m.p. 174°–176° C.

A mixture of benzyl 3-[4-(2-methoxyphenyl)piperazin-1-yl]propylamino-formate dihydrochloride (481 g, 1.05 mol) and potassium carbonate (630 mL, 5.5N, 3.15 mol) in 4L of ethyl acetate was stirred at room temperature for 1 hour. The mixture was washed with water (1×630 mL), treated with silica gel (200 g) and filtered. The filtrate was concentrated under reduced pressure to give benzyl 3-[4-(2-methoxyphenyl)piperazin-1-yl]propylaminoformate (385.9 g, 1.01 mol) as an oil.

A mixture of benzyl 3-[4-(2-methoxyphenyl)piperazin-1-yl]propylamino-formate (384.4 g, I mol) and 10% palladium on carbon (38.4 g) in 3.5L of nitrogen-purged ethanol was hydrogenated at atmospheric pressure for 80 minutes while cooled such that the reaction temperature remained below 30° C. The mixture was filtered and the filtrate was concentrated under reduced pressure to give 3-[4-(2-methoxyphenyl)piperazin-1-yl]propylamine (230.8 g, 0.93 mol) as an oil.

Proceeding as in Example 7, but substituting different starting materials for 1-(2-methoxyphenyl)piperazine, the following compounds of Formula 3 were prepared:

substituting 1-[2,4-di(2,2,2-trifluoroethoxy)phenyl] piperazine gave 3-{4-[2,4-di(2,2,2-trifluoroethoxy) phenyl]piperazin-1-yl}propylamine;

substituting 1-(5-fluoro-2-methoxyphenyl)piperazine gave 3-{4-[5-fluoro-2-methoxyphenyl]piperazin-1-yl}propylamine;

substituting 1-(5-chloro-2-methoxyphenyl)piperazine gave 3-{4-[5-chloro-2-methoxyphenyl]piperazin-1-yl}propylamine;

substituting 1-(2,4-dimethoxyphenyl)piperazine gave 3-{4-[2,4-dimethoxyphenyl]piperazin-1-yl}propylamine;

substituting 1-[2-(2,2,2-trifluoroethoxy)phenyl] piperazine gave 3-{4-[2-(2,2,2-trifluoroethoxy)phenyl] piperazin-1-yl}propylamine;

substituting 1-(2-methylphenyl)piperazine gave 3-[4-(2-methylphenyl)piperazin-1-yl]propylamine;

substituting 1-(2,6-dimethylphenyl)piperazine gave 3-[4-(2,6-dimethylphenyl)piperazin-1-yl]propylamine;

substituting 1-(2-trifluoromethylphenyl)piperazine gave 3-[4-(2-trifluoromethylphenyl)piperazin-1-yl] propylamine;

substituting 1-(2-trifluoromethoxyphenyl)piperazine gave 3-[4-(2-trifluoromethoxyphenyl)piperazin-1-yl] propylamine;

substituting 1-(4-fluoro-2-methoxyphenyl)piperazine gave 3-{4-[4-fluoro-2-methoxyphenyl]piperazin-1-yl}propylamine;

substituting 1-(4-fluorophenyl)piperazine gave 3-{4-[4-fluorophenyl]-piperazin-1-yl}propylamine;

substituting 1-phenylpiperazine gave 3-(4-phenylpiperazin-1-yl)propylamine;

substituting 1-(3-methoxyphenyl)piperazine gave 3-[4-(3-methoxyphenyl)-piperazin-1-yl]propylamine;

substituting 1-(2-bromo-4-fluorophenyl)piperazine gave 3-[4-(2-bromo-4-fluorophenyl)piperazin-1-yl]propylamine;

substituting 1-(2-ethoxyphenyl)piperazine gave 3-[4-(2-ethoxyphenyl)-piperazin-1-yl]propylamine;

substituting 1-(2-isopropylphenyl)piperazine gave 3-[4-(2-isopropylphenyl)-piperazin-1-yl]propylamine;

substituting 1-(2-ethylphenyl)piperazine gave 3-[4-(2-ethylphenyl)-piperazin-1-yl]propylamine;

substituting 1-(4-methyl-2-methoxyphenyl)piperazine gave 3-[4-(4-methyl-2-methoxyphenyl)piperazin-1-yl] propylamine;

substituting 1-(2-benzylphenyl)piperazine gave 3-[4-(2-benzylphenyl)-piperazin-1-yl]propylamine;

substituting 1-(4-benzyloxy-2-methoxyphenyl)piperazine gave 3-[4-(4-benzyloxy-2-methoxyphenyl)piperazin-1-yl]propylamine;

substituting 1-(2-neopentoxyphenyl)piperazine gave 3-[4-(2-neopentoxyphenyl)-piperazin-1-yl] propylamine;

substituting 1-biphen-2-ylpiperazine gave 3-(4-biphen-2-ylpiperazin-1-yl)-propylamine;

substituting 1-[2-(2,2,2-trifluoroethoxy)-4-methylphenyl] piperazine gave 3-{4-[2-(2,2,2-trifluoroethoxy)-4-methylphenyl]piperazin-1-yl}propylamine;

substituting 1-(2-propylphenyl)piperazine gave 3-[4-(2-propylphenyl)-piperazin-1-yl]propylamine; and substituting 1-[2-(2-propynyloxy)phenyl]piperazine gave 3-{4-[2-(2-propynyloxy)-phenyl]piperazin-1-yl}propylamine.

EXAMPLE 8

3-[4-(2-Fluorophenyl)piperazin-1-yl]propylamine

The following is the preparation of a compound of Formula 3 in which R¹ is fluoro, R² is hydro and R⁹ is amino.

A mixture of N-(3-bromopropyl)phthalimide (2.84 g, 10.6 mmol), 1-(2-fluorophenyl)piperazine hydrochloride (2.35 g, 10.84 mmol) and potassium carbonate (1.52 g, 11 mmol) in 20 mL of DMF was stirred at 70° C. for 4.5 hours. The mixture was allowed to cool to room temperature and then partitioned between water and diethyl ether. The ether layer was separated, washed with brine, dried (MgSO₄) and concentrated. The residue was crystallized from hexanes/ethyl acetate (8:1) to give 3-[4-(2-fluorophenyl)piperazin-1-yl]-propylphthalimide (3.04 g, 8.3 mmol).

A mixture of 3-[4-(2-fluorophenyl)piperazin-1-yl] propylphthalimide (1.87 g, 5.09 mmol) and hydrazine hydrate (305 mg, 6.11 mol) in 10L of ethanol was heated at 90° C. for 2 hours. The mixture was allowed to cool to room temperature and then diluted with 4 mL of ethyl acetate and 60 mL of diethyl ether. The mixture was filtered and the solvents were removed by evaporation to give 3-[4-(2-fluorophenyl)piperazin-1-yl]propylamine (574 g, 2.42 mmol).

Proceeding as in Example 8, but substituting different starting materials for 1-(2-fluorophenyl)piperazine hydrochloride, the following compounds of Formula 3 were prepared:

substituting 1-(2-cyclopropylphenyl)piperazine gave 3-[4-(2-cyclopropylphenyl)-piperazin-1-yl] propylamine;

substituting 1-(2-ethylphenyl)piperazine gave 3-[4-(2-ethylphenyl)-piperazin-1-yl]propylamine;

substituting 1-(2,3-dimethylphenyl)piperazine gave 3-[4-(2,3-dimethylphenyl)-piperazin-1-yl]propylamine;

substituting 1-(2-methylthiophenyl)piperazine gave 3-[4-(2-methylthiophenyl)-piperazin-1-yl]propylamine;

substituting 1-(2-cyanophenyl)piperazine gave 3-[4-(2-cyanophenyl)-piperazin-1-yl]propylamine; and substituting 1-(2-oxazol-2-ylphenyl)piperazine gave 3-[4-(2-oxazol-2-ylphenyl)-piperazin-1-yl]propylamine.

EXAMPLE 9

3-[4-(2-Methoxyphenyl)piperazin-1-yl]propylamine

The following is the preparation of a compound of Formula 3 in which R¹ is methoxy, R² is hydro and R⁹ is amino.

A mixture of 1-(2-methoxyphenyl)piperazine hydrochloride (22 g, 96.2 mmol), acrylamide (7.5 g, 106 mmol) and potassium carbonate (20 mL, 5M, 100 mmol) in 110 mL of water was heated at 80° C. for 2 hours to give a suspension. The suspension was allowed to cool to room temperature and filtered. The filtered residue was washed with water (3×30 mL) and dried under reduced pressure at 85° C. for 16 hours to give 3-[4-(2-methoxyphenyl)-piperazin-1-yl] propionamide (22.67 g, 86.1 mol), m.p. 145°–146° C.

3-[4-(2-Methoxyphenyl)piperazin-1-yl]propionamide (3 g, 11.4 mmol) was suspended in 30 mL of freshly distilled THF and borane-tetrahydrofuran complex (17.5 mL, 1M in THF, 17.5 mmol) was added at a rate such that the reaction temperature remained below 26° C. The mixture was stirred at gentle reflux (67° C.) for 6.5 hours, with additional borane-tetrahydrofuran complex (6 mL, 4 mL and 4 mL) added after 1, 3.5 and 5 hours, respectively. The mixture was cooled to 22° C. and then hydrochloric acid (20 mL, 6N, 120 mmol) was added at a rate such that the reaction temperature did not exceed 35° C. The mixture was heated at reflux for 20 minutes and cooled to room temperature and then 50% sodium hydroxide was added at a rate such that the reaction temperature did not exceed 60° C. The aqueous layer was separated and extracted with THF (2×25 mL). The combined organic layers were dried (K₂CO₃) and filtered. The filtrate was concentrated under reduced pressure to give 3-[4-(2-methoxyphenyl)-piperazin-1-yl]propylamine (2.5 g, 10 mmol) as an oil.

EXAMPLE 10

3-[4-(2-Methoxyphenyl)piperazin-1-yl]-1-propanol

The following is the preparation of a compound of Formula 3 in which R¹ is methoxy, R² is hydro and R³ is hydroxy.

A mixture of 3-bromopropanol (10.5 mL, 116 mmol), 1-(2-methoxyphenyl)piperazine (21 g, 109.23 mmol), sodium iodide (16.4 g, 109 mmol), potassium carbonate (38 g, 275 mmol) in 300 mL of acetonitrile was heated at reflux for 3 hours. The mixture was cooled and filtered. The filtrate was washed with saturated sodium chloride, dried (MgSO₄)

and concentrated. The residue was purified by column chromatography eluting with 5% methanol/methylene chloride. Product fractions were combined and concentrated to give 3-[4-(2-methoxyphenyl)piperazin-1-yl]-1-propanol (24.5 g, 97.86 mmol), m.p. 88°–89° C.

Proceeding as in Example 10, but substituting other starting materials for 1-(2-methoxyphenyl)piperazine, the following compounds of Formula 3 were prepared:

substituting 1-(5-chloro-2-methoxyphenyl)piperazine gave 3-[4-(5-chloro-2-methoxyphenyl)piperazin-1-yl]-1-propanol;

substituting 1-[2-(2,2,2-trifluoroethoxy)phenyl]piperazine gave 3-{4-[2-(2,2,2-trifluoroethoxy)phenyl]piperazin-1-yl}-1-propanol, m.p. 94°–96° C., substituting 1-(5-fluoro-2-methoxyphenyl)piperazine gave 3-[4-(5-fluoro-2-methoxyphenyl)piperazin-1-yl]-1-propanol;

substituting 1-(4-fluoro-2-methoxyphenyl)piperazine gave 3-[4-(4-fluoro-2-methoxyphenyl)piperazin-1-yl]-1-propanol;

substituting N-(2-piperazin-1-ylphenyl) trifluoroacetamide gave 3-[4-(2-trifluoroacetylaminophenyl)piperazin-1-yl]-1-propanol;

substituting 1-(2-nitrophenyl)piperazine gave 3-[4-(2-nitrophenyl)-piperazin-1-yl]-1-propanol; and substituting N-(2-piperazin-1-ylphenyl)acetamide gave 3-[4-(2-acetylaminophenyl)piperazin-1-yl]-1-propanol.

EXAMPLE 11

{3-[4-(2-Methoxyphenyl)piperazin-1-yl]propyl}(methyl)amine

The following is the preparation of a compound of Formula 3 in which $R^1$ is methoxy, $R^2$ is hydro and $R^9$ is methylamino.

A solution of benzyl 3-[4-(2-methoxyphenyl)piperazin-1-yl]propylamino-formate (980 mg, 2.56 mmol), prepared as in Example 7, in 5 mL of DMF was cooled to 0° C. and sodium hydride (200 mg, 5.12 mmol) was added. The mixture was stirred at 0° C. for 20 minutes and then iodomethane (0.2 mL, 3.07 mmol) was added. The mixture was stirred at room temperature for approximately 60 hours. The mixture was diluted with water and extracted with ethyl acetate (3×20 mL). The combined extract was washed with brine (2×), dried (MgSO$_4$), filtered and concentrated. The residue was purified on silica gel by column chromatography eluting with 5% methanol/methylene chloride to give {3-[4-(2-methoxyphenyl)-piperazin-1-yl]propyl}(methyl)aminoformate (710 mg, 1.79 mmol).

A mixture of {3-[4-(2-methoxyphenyl)piperazin-1-yl]propyl}(methyl)amino-formate (500 mg, 1.26 mmol) and 10% palladium on carbon (92 mg) in 15 mL of ethanol was stirred at room temperature under a hydrogen atmosphere for approximately 15 hours. The mixture was filtered and concentrated to give {3-[4-(2-methoxyphenyl)piperazin-1-yl]propyl}(methyl)amine (264 mg, 1 mmol) as an oil.

EXAMPLE 12

3-[4-(2-Methoxyphenyl)piperazin-1-yl]-1-propanethiol

The following is the preparation of a compound of Formula 3 in which $R^1$ is methoxy, $R^2$ is hydro and $R^9$ is mercapto.

A solution of 3-[4-(2-methoxyphenyl)piperazin-1-yl]-1-propanol (2.16 g, 8.6 mmol), prepared as in Example 10, in 20 mL of methylene chloride was cooled to 0° C. under nitrogen and triethylamine (1.45 mL, 10.5 mmol) and methanesulfonyl chloride (0.74 mL, 9.5 mmol) in 20 mL of methylene chloride were added. The mixture was allowed to warm to room temperature and stirred for 45 minutes. The mixture was poured into aqueous sodium bicarbonate and extracted with ethyl acetate. The extract was washed with brine, dried (K$_2$CO$_3$) and concentrated by rotary evaporation. The residue was dissolved in 10 mL of DMF and the solution was added to a mixture of potassium thioacetate (1.18 g, 10.3 mmol) and sodium iodide (65 mg, 0.4 mmol) in 20 mL of DMF. The mixture was purged with nitrogen under a vacuum and then heated at 50° C. for 20 hours. The mixture was allowed to cool to room temperature and partitioned between water and hexanes/ethyl acetate (1:1). The organic layer was separated, washed with water and then brine, dried (Na$_2$SO$_4$) and concentrated. The residue was purified on silica gel by column chromatography eluting with hexanes/ethyl acetate (2:1) to give 3-[4-(2-methoxyphenyl)piperazin-1-yl]propylthioacetate (1.43 g, 4.6 mmol).

A mixture of 3-[4-(2-methoxyphenyl)piperazin-1-yl]propylthioacetate (495 mg, 1.61 mmol) and sodium borohydride (291 mg, 7.7 mmol) in 15 mL of ethanol was stirred for approximately 12 hours. The volatile were removed in vacuo and the residue was suspended in methylene chloride. The suspension was filtered and the collected residue dried to give 3-[4-(2-methoxyphenyl)-piperazin-1-yl]-1-propanethiol (315 mg, 1.18 mmol).

EXAMPLE 13

2-Chloro-N,N-dimethylnicotinamide

The following is the preparation of a compound of Formula 2 in which t is 0, L is chloro, Y is N, Z is CH and $R^3$ is dimethylaminocarbonyl.

A mixture of 2-chloronicotinic acid (1 kg, 6.35 mmol) and thionyl chloride (575 mL, 7.88 mmol) 30 mL of DMF and 3.2L of toluene was warmed slowly to 70° C. and heated at 70° C. for 30 minutes. The mixture was allowed to cool to approximately 40° C. and then added to a 40% solution of aqueous dimethylamine (3.2L, 25.5 mmol) at 10° C. such that the reaction mixture did not exceed 28° C. An additional 30 minutes was allowed and then the aqueous layer was separated and extracted with toluene (2×1L). Combined organic layers were dried (Na$_2$SO$_4$), filtered and concentrated under reduced pressure. The residue was dissolved in 2L of ethyl acetate and 4L of hexanes were added slowly to give a precipitate. The mixture was aged for 16 hours and then an additional 1L of hexanes was added. The mixture was cooled in an ice bath for 2 hours and filtered. The filtered residue was washed with 20% ethyl acetate/hexanes (1×1L) and dried under a stream of air to give 2-chloro-N, N-dimethyl-nicotinamide (924.5 g, 5.01 mmol), m.p. 66°–67° C.

Proceeding as in Example 13, but substituting different starting materials for dimethylamine and/or 2-chloronicotinic acid, the following compounds of Formula 2 were prepared:

substituting morpholine gave 2-chloro-N-morpholin-4-ylnicotinamide;

substituting pyrrolidine gave 2-chloro-N-pyrrolidin-1-ylnicotinamide;

substituting diethylamine, gave 2-chloro-N,N-diethylnicotinamide;

substituting N,O-dimethylhydoxylamine hydrochloride gave 2-chloro-N-methoxy-N-methylnicotinamide;

substituting 2,6-dichloronicotinic acid gave 2,6-dichloro-N,N-dimethyl-nicotinamide;

substituting 2-chloro-4,6-dimethylnicotinic acid gave 2-chloro-N,N,4,6-tetramethylnicotinamide; and substituting diisopropylamine and 4-chloronicotinic acid gave N,N-diisopropyl-4-chloronicotinamide; and substituting 4-chloronicotinic acid gave 4-chloro-N,N-dimethylnicotinamide.

EXAMPLE 14

2-Chloro-5-iodo-N,N-dimethylnicotinamide

The following is the preparation of a compound of Formula 2 in which t is 1, L is chloro, Y is N, Z is CH, $R^3$ is dimethylaminocarbonyl and $R^4$ is iodo at the 5-position.

A solution of 2-hydroxynicotinic acid (7.17 g, 51.5 mmol) in 100 mL of DMF was treated with N-iodosuccinimide (12.76 g, 56.7 mmol) for approximately 64 hours. The mixture was concentrated under reduced pressure and the residue was suspended in approximately 70 mL of dichloroethane. Thionyl chloride (15 mL, 20.8 mmol) was slowly added to the suspension and the mixture was heated at reflux for 2 hours. The mixture was distilled until approximately 70 mL of distillate was collected. The residue was allowed to cool to room temperature and then dissolved in 70 mL of methylene chloride. The solution was cooled under nitrogen to 0° C. and treated with triethylamine (23 mL, 156 mmol). Dimethylamine hydrochloride (4.6 g, 56 mmol) was added and the mixture was stirred at approximately 0° C. for 0.5 hours. The mixture was filtered and the filtrate was partitioned between aqueous sodium bicarbonate and methylene chloride. The methylene chloride layer was separated, washed with brine, dried ($Na_2SO_4$) and concentrated. The residue was purified on silica gel by column chromatography eluting with hexanes/ethyl acetate (5:1) to give 2-chloro-5-iodo-N,N-dimethyl-nicotinamide (5.17 g, 16.7 mmol).

EXAMPLE 15

2-Chloro-5-cyano-N,N-dimethylnicotinamide

The following is the preparation of a compound of Formula 2 in which t is 1, L is chloro, Y is N, Z is CH, $R^3$ is dimethylaminocarbonyl and $R^4$ is cyano at the 5-position.

A mixture of 2-chloro-5-iodo-N,N-dimethylnicotinamide (1.54 g, 5 mmol), prepared as in Example 14, and lithium cyanide (0.5M in DMF, 20 mL, 10 mmol) was distilled at reduced pressure. The residue was suspended in 1,4,7,10-tetraoxacyclo-dodecane (0.2 mL, 1.25 mmol) in 50 mL of benzene and the mixture was distilled under nitrogen until a forefraction of approximately 5 mL had collected. The suspension was allowed to cool and then tetrakis(triphenylphosphine)palladium(0) (2.44 g, 2.1 mmol) was added. The mixture was stirred at 40° C. under nitrogen for 1 week, allowed to cool to room temperature and partitioned between aqueous sodium bicarbonate and ethyl acetate. The aqueous layer was extracted with diethyl ether and the extract was washed with brine, dried ($Na_2SO_4$) and concentrated. The residue was purified on silica gel by column chromatography eluting with hexanes/ethyl acetate (5:1) to give 2-chloro-5-cyano-N,N-dimethylnicotinamide (0.57 g, 2.72 mmol), m.p. 148°–153° C.

EXAMPLE 16

2-Chloro-N,N,5-trimethylnicotinamide

The following is the preparation of a compound of Formula 2 in which t is 1, L is chloro, Y is N, Z is CH, $R^3$ is dimethylaminocarbonyl and $R^4$ is methyl at the 5-position.

A solution of 2-chloro-5-iodo-N,N-dimethylnicotinamide (0.385 g, 1.24 mmol), prepared as in Example 14, in 10 mL of THF was distilled to remove volatile gases. The residual solution was cooled −90° C. and then tert-butyllithium (1.9 mL, 2.48 mmol) was added over 3 to 5 minutes. Iodomethane (0.23 mL, 3.72 mmol) was added and the mixture was allowed to warm to room temperature. The mixture was partitioned between aqueous sodium carbonate (pH 10) and hexanes and the aqueous layer was extracted with ethyl acetate. The extract was washed with brine, dried ($Na_2SO_4$) and concentrated. The residue was purified on silica gel by column chromatography eluting with hexanes/ethyl acetate (3:1) to give 2-chloro-N,N,5-trimethylnicotinamide (0.152 g, 0.78 mmol), m.p. 117°–119° C.

EXAMPLE 17

4-Chloro-N,N-dimethyl-5-pyrimidinecarboxamide

The following is the preparation of a compound of Formula 2 in which t is 0, L is chloro, Y and Z are each N and $R^3$ is dimethylaminocarbonyl.

A mixture of N,N',N"-methylidynetrisformamide (25 g, 172 mmol), diethyl malonate (26 mL, 172 mmol) and p-toluenesulfonic acid monohydrate (3.2 g, 17 mmol) was heated at 180° C. for 1.5 hours and then allowed to cool to room temperature. The mixture was stirred vigorously with diethyl ether to give a precipitate. The precipitate was isolated and dissolved in 150 mL of hot water. The solution was allowed to cool to give precipitate. The precipitate was dried to give ethyl 4-hydroxy-5-pyrimidinecarboxylic acid ester (7 g, 41.7 mmol), m.p. 187°–188° C.

A mixture of ethyl 4-hydroxy-5-pyrimidinecarboxylic acid ester (1.5 g, 8.9 mmol), and potassium hydroxide (1.2 g, 21.4 mmol) in 10 mL of ethanol was stirred under nitrogen at 75° C. for approximately 20 hours. The mixture was diluted with 10 mL of diethyl ether, cooled to 0° C. and acidified to pH 1 with 12M hydrochloric acid to give a precipitate. The precipitate was isolated by filtration and dried in vacuo to give 4-hydroxy-5-pyrimidinecarboxylic acid (0.88 g, 6.3 mmol).

A mixture of 4-hydroxy-5-pyrimidinecarboxylic acid (0.88 g, 6.3 mmol) in 5 drops of DMF and 6 mL of thionyl chloride was heated at reflux for 3 hours. The mixture was concentrated and the residue was dissolved in methylene chloride. A mixture of the residue, dimethylamine hydrochloride (0.62 g, 7.6 mmol) and triethylamine (4.5 mL, 31.5 mmol) in 50 mL of methylene chloride was stirred at 0° C. for 0.5 hours. The mixture was poured into water and aqueous sodium bicarbonate. The mixture was extracted with methylene chloride (2×30 mL) and the extract was washed with brine, dried ($Na_2SO_4$) and concentrated by rotary evaporation to give 4-chloro-N,N-dimethyl-5-pyrimidinecarboxamide (0.66 g, 3.6 mmol) as an oil.

EXAMPLE 18

3-Acetyl-2-chloropyridine

The following is the preparation of a compound of Formula 2 in which t is 0, L is chloro, Y is N, Z is CH and $R^3$ is acetyl.

A mixture of 2-chloronicotinic acid (20 g, 0.127 mmol) and oxalyl chloride (13.3 mL, 0.152 mmol) in 2 drops of DMF and 200 mL of methylene chloride was stirred at room temperature for approximately 14 hours. The mixture was stirred at reflux temperature for 1 hour. The solution was cooled and partitioned between 100 mL of ice-cold aqueous sodium bicarbonate and 300 mL of methylene chloride. The organic layer was washed with brine, dried ($Na_2SO_4$) and concentrated to give 2-chloronicotinic acid chloride (8.8 g, 49.5 mmol).

A mixture of 2-chloronicotinic acid chloride (8.8 g, 49.5 mmol), tetramethyltin (5.5 mL, 40 mmol) and bis(benzonitrile)palladium(II) chloride (0.385 g) in 20 mL of hexamethylphosphoramide was stirred at room temperature for 20 hours. The mixture was stirred with 50 mL of 10% potassium fluoride and then poured into 50 mL of water. The mixture was extracted with diethyl ether (4×50 mL) and the combined extracts were washed with water, saturated sodium bicarbonate and sodium chloride, dried ($Na_2SO_4$) and concentrated. The residue was purified on silica gel by column chromatography eluting with hexanes/ethyl acetate (3:1) to give 3-acetyl-2-chloropyridine (4.2 g, 27 mmol).

EXAMPLE 19

2-Chloro-3-pyridyl cyclopropyl ketone

The following is the preparation of a compound of Formula 2 in which t is 0, L is chloro, Z is CH and $R^3$ is cyclopropyl.

A mixture of cyclopropyltributyltin (0.5 g, 1.51 mmol) in 3 mL of THF was cooled to −78° C. and then n-butyllithium (0.604 mL, 2.5M in hexanes, 1.51 mmol) was added. The mixture was stirred at 0° C. for 0.5 hours. A mixture of copper(I) iodide (0.142 g, 0.75 mmol) in THF was cooled to −40° C. and the mixture containing the cyclopropyltributyltin was added. The mixture was stirred for 45 minutes and then 2-chloronicotinic acid chloride (0.265 g, 1.51 mmol) was added dropwise. The mixture was stirred at −40° C. for 1.5 hours and allowed to warm to room temperature. The mixture was quenched with water, diluted with methylene chloride, filtered and the aqueous layer was extracted with methylene chloride (2×30 mL). The combined organic layers were dried ($Na_2SO_4$) and concentrated. The residue was purified on silica gel by flash chromatography eluting with hexanes/ethyl acetate (85:15) to give 2-chloro-3-pyridyl cyclopropyl ketone (0.15 g, 0.83 mmol) as an oil.

EXAMPLE 20

1-(2-Chloro-3-pyridyl)-2,2-dimethylpropan-1-one

The following is the preparation of a compound of Formula 2 in which t is 0, L is chloro, Z is CH and $R^3$ is tert-butyl.

A mixture of copper(I) iodide (1.18 g, 6.2 mmol) in 5 mL of THF was cooled to −40° C. and then tert-butyllithium (8.85 mL, 1.4M, 12.4 mmol) was added. The mixture was stirred for 1 hour and 2-chloronicotinic acid chloride (2 g, 11.3 mmol) was added dropwise. The mixture was stirred at −40° C. for 1.5 hours and then allowed to warm to room temperature. The mixture was quenched with water and then diluted with ethyl acetate. The mixture was filtered, washed with water (2×10 mL) and brine, dried ($Na_2SO_4$) and concentrated. The residue was purified on silica gel by flash chromatography eluting with hexanes/ethyl acetate (85:15) to give 1-(2-chloro-3-pyridyl)-2,2-dimethylpropan-1-one (1.735 g, 8.8 mmol) as an oil.

EXAMPLE 21

2-{3-[4-(2-methoxyphenyl)piperazin-1-yl]propylamino}-N,N-dimethylnicotinamide hydrochloride The following is the preparation of a compound of Formula I in which p and t are each 0, X is NH, Y is N, Z is CH, $R^1$ is methoxy, $R^2$ is hydro and $R^3$ is dimethylaminocarbonyl.

A mixture of 2-chloro-N,N-dimethylnicotinamide (174.3 g, 0.94 mmol), prepared as in Example 13, 3-[4-(2-methoxyphenyl)piperazin-1-yl]propylamine (224 g, 0.9 mmol), prepared as in Example 7, and potassium carbonate (250.5 g, 1.81 mmol) in 4 L of xylenes was heated at gentle reflux (133° to 136° C.) for 39 hours. The mixture was allowed to cool to 50° C. and then 1 L of water was added. The organic layer was separated, washed with water (2×500 mL) and concentrated under reduced pressure. The residue was dissolved in 6 L of ethyl acetate and the solution was washed with water (3×1 L) and saturated sodium chloride (2×250 mL), dried ($MgSO_4$) and filtered. The filter was rinsed with 1 L of ethyl acetate and the combined filtrate was concentrated to approximately 4.8 L. A solution of 3.8N hydrochloric acid (175 mL, 0.67 mmol) in ethanol was added and the mixture was aged at room temperature for 90 minutes and then filtered. The filtered residue was washed with ethyl acetate (4×500 mL), dried under reduced pressure at 79° C. for 18 hours to give 2-{3-[4-(2-methoxyphenyl)piperazin-1-yl]propylamino}-N,N-dimethylnicotinamide hydrochloride (259.4 g, 0.6 mmol), m.p. 204°–206° C. Anal.: Calcd. for $C_{22}H_{31}N_5O_2.HCl$: C, 60.89; H, 7.43; N, 16.14%; Found: C, 61.14; H, 7.46; N, 15.96%.

Proceeding as in Example 21, but substituting different starting materials for N,N-dimethyl-2-chloronicotinamide and/or 3-[4-(2-methoxyphenyl)-piperazin-1-yl]propylamine the following compounds Formula I were prepared:

substituting 3-(4-phenylpiperazin-1-yl)propylamine gave 2-[3-(4-phenyl-piperazin-1-yl)propylamino]-N,N-dimethylnicotinamide hydrochloride, m.p. 100° C. (dec); Anal.: Calcd. for $C_{21}H_{31}N_5O.(HCl)_2$: C, 58.03; H, 5.51; N, 13.98%; Found: C, 55.54; H, 7.24; N, 14.32%;

substituting 3-[4-(4-fluorophenyl)piperazin-1-yl]propylamine gave 2-{3-[4-(4-fluorophenyl)piperazin-1-yl]propylamino}-N,N-dimethylnicotinamide hydrochloride, m.p. 63°–68° C.; Anal.: Calcd. for $C_{21}H_{30}FN_5O.(HCl)_2$: C, 52.49; H, 6.98; N, 13.54%; Found: C, 52.53; H, 6.84; N, 13.30%;

substituting 3-[4-(3-methoxyphenyl)piperazin-1-yl]propylamine gave 2-{3-[4-(3-methoxyphenyl)piperazin-1-yl]propylamino}-N,N-dimethylnicotinamide hydrochloride, m.p. 75° C. (dec); Anal.: Calcd. for $C_{22}H_{31}N_5O_2.(HCl)_{2.6}$: C, 53.71; H, 6.98; N, 13.62%; Found: C, 53.62; H, 7.11; N, 13.56%;

substituting 3-[4-(2-bromo-4-fluorophenyl)piperazin-1-yl]propylamine gave 2-{3-[4-(2-bromo-4-fluorophenyl)piperazin-1-yl]propylamino}-N,N-dimethylnicotinamide oxalate, m.p. 122°–125° C.; Anal.: Calcd. for $C_{21}H_{27}FBrN_5O.(C_2H_2O_4)_2$: C, 46.59; H, 4.85; N, 10.87%; Found: C, 46.48; H, 4.84; N, 10.80%;

substituting 3-[4-(2-methylphenyl)piperazin-1-yl]propylamine gave N,N-dimethyl-2-{3-[4-(2-methylphenyl)piperazin-1-yl]propylamino}nicotinamide hydrochloride, m.p. 68° C. (dec); Anal.: Calcd. for $C_{22}H_{31}N_5O.(HCl)_{2.5}.(H_2O)_{1.5}$: C, 52.88; H, 7.36; N, 14.02%; Found: C, 52.99; H, 7.70; N, 14.07%;

substituting 3-[4-(2,6-dimethylphenyl)piperazin-1-yl]propylamine gave N,N-dimethyl-2-{3-[4-2,6-dimethylphenyl)piperazin-1-yl]propylamino}nicotinamide hydrochloride, m.p. 88°–125° C.; Anal.: Calcd. for $C_{23}H_{33}N_5O.HCl.(H_2O)_{0.5}$: C, 62.64; H, 8.00; N, 15.88%; Found: C, 62.39; H, 7.82; N, 15.62%;

substituting 3-[4-(2-trifluoromethylphenyl)piperazin-1-yl]propylamine and recrystallizing from a solution of oxalic acid in alcohol gave 2-{3-[4-(2-trifluoromethylphenyl)piperazin-1-yl]propylamino}-N,N-dimethylnicotinamide oxalate, m.p. 133°–134° C.; Anal.: Calcd. for $C_{22}H_{28}F_3N_5O.(C_2H_2O_4)_{1.5}$: C, 52.63; H, 5.48; N, 12.27%; Found: C, 52.85; H, 5.58; N, 12.21%;

substituting 3-[4-(2-propylphenyl)piperazin-1-yl]propylamine and recrystallizing from a solution of oxalic acid in alcohol gave 2-{3-[4-(2-propylphenyl)-piperazin-1-yl]propylamino}-N,N-dimethylnicotinamide oxalate, m.p. 127°–128° C.; Anal.: Calcd. for $C_{24}H_{35}N_5O_2.C_2H_2O_4$: C, 62.51; H, 7.46; N, 14.02%; Found: C, 62.50; H, 7.33; N, 13.95%;

substituting 3-[4-(2-isopropylphenyl)piperazin-1-yl]propylamine and recrystallizing from a solution of oxalic acid in alcohol gave 2-{3-[4-(2-isopropylphenyl)piperazin-1-yl]propylamino}-N,N-dimethylnicotinamide oxalate, m.p. 119°–121° C.; Anal.: Calcd. for $C_{24}H_{35}N_5O.(C_2H_2O_4)_{2.5}$: C, 54.88; H, 6.35; N, 11.03%; Found: C, 54.82; H, 6.34; N, 11.01%;

substituting 3-(4-biphen-2-ylpiperazin-1-yl)propylamine gave N,N-dimethyl-2-[3-(4-biphen-2-ylpiperazin-1-yl)propylamino]nicotinamide hydrochloride, m.p. 196°–197° C.; Anal.: Calcd. for $C_{27}H_{33}N_5O.(HCl)_2(H_2O)_{0.25}$: C, 62.78; H, 6.83; N, 13.55%; Found: C, 65.57; H, 7.04; N, 13.27%;

substituting 3-[4-(2-benzylphenyl)piperazin-1-yl]propylamine and recrystallizing from a solution of oxalic acid in alcohol gave 2-{3-[4-(2-benzylphenyl)-piperazin-1-yl]propylamino}-N,N-dimethylnicotinamide oxalate, m.p. 127°–130° C.; Anal.: Calcd. for $C_{28}H_{35}N_5O.C_2H_2O_4$: C, 65.79; H, 6.81; N, 12.79%; Found: C, 65.91; H, 6.72; N, 12.71%;

substituting 2-chloro-N-morpholin-4-ylnicotinamide gave 2-{3-[4-(2-methoxy-phenyl)piperazin-1-yl]propylamino}-N-morpholin-4-ylnicotinamide hydrochloride, m.p. 69°–70° C.; Anal.: Calcd. for $C_{24}H_{33}N_5O_3.(HCl)_3$: C, 52.51; H, 6.61; N, 12.76%; Found: C, 52.53; H, 6.94; N, 13.77%;

substituting 2,6-dichloro-N,N-dimethylnicotinamide gave 6-chloro-2-{3-[4-(2-methoxyphenyl)piperazin-1-yl]propylamino}-N,N-dimethylnicotinamide hydrochloride, m.p. 233°–234° C.; Anal.: Calcd. for $C_{22}H_{30}ClN_5O_2.HCl$: C, 56.41; H, 6.67; N, 14.95%; Found: C, 56.64; H, 6.64; N, 15.13%;

substituting 3-[4-(5-fluoro-2-methoxyphenyl)piperazin-1-yl]propylamine gave 2-{3-[4-(5-fluoro-2-methoxyphenyl)piperazin-1-yl]propylamino}-N,N-dimethyl-nicotinamide hydrochloride, m.p. 124°–128° C.; Anal.: Calcd. for $C_{22}H_{30}FN_5O_2(HCl)_2.(C_2H_6O)_{0.5}$: C, 50.42; H, 6.62; N, 12.78%; Found: C, 50.44; H, 6.94; N, 12.72%;

substituting 3-[4-(5-chloro-2-methoxyphenyl)piperazin-1-yl]propylamine and recrystallizing from a solution of tartaric acid in alcohol gave 2-{3-[4-(5-chloro-2-methoxyphenyl)piperazin-1-yl]propylamino}-N,N-dimethyl-nicotinamide tartrate, m.p. 59°–75° C.; Anal.: Calcd. for $C_{22}H_{30}ClN_5O_2.C_4H_6O_6.H_2O$: C, 53.65; H, 6.23; N, 12.03%; Found: C, 50.45; H, 6.54; N, 12.23%;

substituting 2-chloro-3-pyridyl cyclopropyl ketone and recrystallizing from a solution of maleic acid in alcohol gave cyclopropyl 2-{3-[4-(2-methoxyphenyl)-piperazin-1-yl]propylamino}-3-pyridyl ketone maleate, m.p. 159°–161° C.; Anal.: Calcd. for $C_{23}H_{30}N_4O_2.C_4H_4O_4$: C, 63.51; H, 6.71; N, 10.97%; Found: C, 63.52; H, 6.59; N, 10.86%;

substituting 3-{4-[2,4-dimethoxyphenyl]piperazin-1-yl}propylamine gave 2-{3-[4-(2,4-dimethoxyphenyl)piperazin-1-yl]propylamino}-N,N-dimethyl-nicotinamide hydrochloride; Anal.: Calcd. for $C_{23}H_{33}N_5O_2.(HCl)_2.(C_4H_8O)_{0.5}$: C, 55.19; H, 7.05; N, 13.99%; Found: C, 52.90; H, 7.39; N, 12.24%;

substituting 2-chloro-N-pyrrolidin-1-ylnicotinamide gave 2-{3-[4-(2-methoxyphenyl)piperazin-1-yl]propylamino}-N-pyrrolidin-1-yl-nicotinamide hydrochloride, m.p. 223°–224° C.; Anal.: Calcd. for $C_{24}H_{33}N_5O_2.HCl$: C, 65.66; H, 7.44; N, 15.22%; Found: C, 62.49H, 7.55; N, 15.15%;

substituting 1-(2-chloro-3-pyridyl)-2,2-dimethylpropan-1-one and recrystallizing from a solution of maleic acid in alcohol gave 1-(2-{3-[4-(2-methoxyphenyl)-piperazin-1-yl]propylamino}-3-pyridyl)-2,2-dimethylpropan-1-one maleate, m.p. 122°–126° C.; Anal.: Calcd. for $C_{24}H_{34}N_4O_2.C_4H_4O_4.(H_2O)_{0.4}$: C, 62.99; H, 7.32; N, 10.49%; Found: C, 63.01; H, 7.37; N, 10.55%;

substituting 3-[4-(4-benzyloxy-2-methoxyphenyl)piperazin-1-yl]propylamine and deprotecting gave 2-{3-[4-(4-hydroxy-2-methoxyphenyl)piperazin-1-yl]propyl-amino}-N,N-dimethylnicotinamide hydrochloride, m.p. 165 (dec)°C.; Anal.: Calcd. for $C_{22}H_{31}N_5O_3.(HCl)_3$: C, 50.53; H, 6.55; N, 13.39%; Found: C, 50.68; H, 6.56; N, 13.02%;

substituting 2-chloro-N,N-diethylnicotinamide gave 2-{3-[4-(2-methoxyphenyl)-piperazin-1-yl]propylamino}-N,N-diethylnicotinamide hydrochloride, m.p. 125° C. (dec); Anal.: Calcd. for $C_{24}H_{35}N_5O_2.(HCl)_2.(H_2O)_{0.7}$: C, 56.39; H, 7.57; N, 13.70%; Found: C, 56.40; H, 7.66; N, 13.63%;

substituting 3-[4-(4-fluoro-2-methoxyphenyl)piperazin-1-yl]propylamine gave 2-{3-[4-(4-fluoro-2-methoxyphenyl)piperazin-1-yl]propylamino}-N,N-dimethyl-nicotinamide hydrochloride, m.p. 228°–229° C.; Anal.: Calcd. for $C_{22}H_{30}FN_5O_2.HCl$: C, 54.32; H, 6.21; N, 14.39%; Found: C, 54.18; H, 6.20; N, 14.19%;

substituting 2-chloro-5-cyano-N,N-dimethylnicotinamide gave 5-cyano-2-{3-[4-(2-methoxyphenyl)piperazin-1-yl]propylamino}-N,N-dimethylnicotinamide oxalate, m.p. 126°–128° C.; Anal.: Calcd. for $C_{23}H_{30}N_6O_2.(C_2H_2O_4)_{1.5}$: C, 56.01; H, 5.97; N, 15.07%; Found: C, 55.72; H, 6.02; N, 14.88%;

substituting 2-chloro-N,N, 5-trimethylnicotinamide and 3-{4-[2-(2,2,2-trifluoroethoxy)-4-methylphenyl]piperazin-1-yl}propylamine gave 2-(3-{4-[2-(2,2,2-trifluoroethoxy)-4-methylphenyl]piperazin-1-yl}propylamino)-N,N,5-trimethylnicotinamide hydrobromide, m.p. 207°–208° C.; Anal.: Calcd. for $C_{25}H_{34}F_3N_5O_2.HBr.(H_2O)_{0.25}$: C, 51.86; H, 6.18; N, 12.01%; Found: C, 51.84; H, 6.13; N, 12.02%;

substituting 3-acetyl-2-chloropyridine gave 3-acetyl-2-{3-[4-(2-methoxyphenyl)-piperazin-1-yl]propylamino}pyridine hydrochloride, m.p. 190°–191° C.; Anal.: Calcd. for $C_{21}H_{28}N_4O_2.(HCl)_{1.2}$: C, 61.19; H, 7.14; N, 13.59%; Found: C, 61.35; H, 7.16; N, 13.69%;

substituting 2-chloro-N,N-dimethylnicotinamide N-oxide and recrystallizing from a solution of oxalic acid in alcohol gave 2-{3-[4-(2-methoxyphenyl)-piperazin-1- yl]propylamino}-N,N-dimethylnicotinamide N-oxide oxalate, m.p. 67°–70° C.; Anal.: Calcd. for $C_{22}H_{31}N_5O_3 \cdot C_2H_8O$: C, 55.25; H, 6.80; N, 13.20%; Found: C, 55.26; H, 6.50; N, 13.24%;

substituting 2-chloro-N,N, 4,6-tetramethylnicotinamide gave 2-{3-[4-(2-methoxyphenyl)piperazin-1-yl] propylamino}-N,N,4,6-tetramethylnicotinamide hydrochloride, m.p. 72°–83° C.; Anal.: Calcd. for $C_{24}H_{35}N_5O_2 \cdot (HCl)_3$: C, 53.88; H, 7.16; N, 13.09%; Found: C, 54.17; H, 7.13; N, 12.85%;

substituting 3-[4-(4-methyl-2-methoxyphenyl)piperazin-1-yl]propylamine and recrystallizing from a solution of oxalic acid in alcohol gave N,N-dimethyl-2-{3-[4-(4-methyl-2-methoxyphenyl)piperazin-1-yl]propylamino}nicotinamide oxalate, m.p. 90°–97° C.; Anal.: Calcd. for $C_{23}H_{33}N_5O_2 \cdot C_2H_2O_4 \cdot C_2H_4O \cdot H_2O$: C, 57.58; H, 7.3; N, 12.62%; Found: C, 57.53; H, 6.96; N, 12.73%;

substituting 2-chloro-N-methoxy-N-methylnicotinamide gave 2-{3-[4-(2-methoxyphenyl)piperazin-1-yl]propylamino}-N-methoxy-N-methylnicotinamide hydrochloride, m.p. 151°–161° C.; Anal.: Calcd. for $C_{22}H_{31}N_5O_3 \cdot (HCl)_{1.5}(H_2O)_{0.3}$: C, 55.79; H, 7.04; N, 14.78%; Found: C, 55.83; H, 6.92; N, 14.69%;

substituting 3-[4-(2-difluoromethoxyphenyl)piperazin-1-yl]propylamine and recrystallizing from a solution of oxalic acid in alcohol gave N,N-dimethyl-2-{3-[4-(2-difluoromethoxyphenyl)piperazin-1-yl]propylamino}nicotinamide oxalate, m.p. 134°–135° C.; Anal.: Calcd. for $C_{22}H_{29}F_2O_2 \cdot C_2H_2O_4 \cdot (C_4H_4O)_{0.33}$: C, 57.58; H, 7.3; N, 12.62%; Found: C, 57.53; H, 6.96; N, 12.73%;

substituting 3-[4-(2-trifluoromethoxyphenyl)piperazin-1-yl]propylamine and recrystallizing from a solution of oxalic acid in alcohol gave 2-{3-[4-(2-trifluoromethoxyphenyl)piperazin-1-yl]propylamino}-N,N-dimethyl-nicotinamide oxalate, m.p. 143°–145° C.; Anal.: Calcd. for $C_{22}H_{28}F_3N_5O_2 \cdot C_2H_2O_4$: C, 53.23; H, 5.58; N, 12.93%; Found: C, 53.42; H, 5.62; N, 12.81%;

substituting 3-[4-(2-ethoxyphenyl)piperazin-1-yl]propylamine and recrystallizing from oxalic acid gave 2-{3-[4-(2-ethoxyphenyl)piperazin-1-yl]propylamino}-N,N-dimethylnicotinamide oxalate, m.p. 138°–140° C.; Anal.: Calcd. for $C_{23}H_{33}N_5O_2 \cdot C_2H_2O_4$: C, 59.87; H, 7.03; N, 13.96%; Found: C, 59.63; H, 7.03; N, 13.72%;

substituting 3-{4-[2,4-di(2,2,2-trifluoroethoxy)phenyl]piperazin-1-yl}propyl-amine gave 2-{3-{4-[2,4-di(2,2,2-trifluoroethoxy)phenyl]piperazin-1-yl}-propylamino}-N,N-dimethylnicotinamide hydrochloride, m.p. 105°–118° C.; Anal.: Calcd. for $C_{25}H_{31}F_6N_5O_3 \cdot (HCl)_3$: C, 44.62; H, 5.09; N, 10.41%; Found: C, 46.84; H, 5.42; N, 10.66%;

substituting 3-{4-[2-(2,2,2-trifluoroethoxy)phenyl]piperazin-1-yl}propylamine gave 2-(3-{4-[2-(2,2,2-trifluoroethoxy)phenyl]piperazin-1-yl}propylamino)-N,N-dimethylnicotinamide hydrochloride, m.p. 122° C. (dec); Anal.: Calcd. for $C_{23}H_{30}F_3N_5O_2 \cdot (HCl)_{2.5} \cdot (C_4H_8O)_{0.1}$: C, 49.70; H, 5.94; N, 12.38%; Found: C, 50.26; H, 6.20; N, 12.59%;

substituting 3-{4-[2-(2,2,2-trifluoroethoxy)phenyl]piperazin-1-yl}propylamine and 2-chloro-N-methoxy-N-methylnicotinamide gave 2-(3-{4-[2-(2,2,2-trifluoroethoxy)phenyl]piperazin-1-yl}propylamino)-N-methoxy-N-methylnicotinamide hydrochloride, m.p. 161°–177° C.; Anal.: Calcd. for $C_{23}H_{30}F_3N_5O_3 \cdot (HCl)_{1.75} \cdot (C_4H_8O)_{0.1}$: C, 55.79; H, 7.04; N, 14.78%; Found: C, 55.83; H, 6.92; N, 14.69%;

substituting 3-[4-(2-isopropoxyphenyl)piperazin-1-yl] propylamine gave 2-{3-[4-(2-isopropoxyphenyl)piperazin-1-yl]propylamino}-N,N-dimethylnicotinamide hydrochloride; Anal.: Calcd. for $C_{24}H_{35}F_3N_5O_2 \cdot (HCl)_2 \cdot (C_4H_{10}O)_{0.3} \cdot (H_2O)_{0.4}$: C, 57.33; H, 7.79; N, 13.26%; Found: C, 57.40; H, 7.79; N, 12.02%;

substituting 3-[4-(2-neopentoxyphenyl)piperazin-1-yl] propylamine gave 2-{3-[4-(2-neopentoxyphenyl)piperazin-1-yl]propylamino}-N,N-dimethylnicotinamide hydrochloride, m.p. 111°–126° C.; Anal.: Calcd. for $C_{26}H_{39}N_5O_2 \cdot HCl$: C, 60.99; H, 7.99; N, 13.68%; Found: C, 60.82; H, 7.93; N, 13.40%;

substituting 3-[4-(2-cyclopropylmethoxyphenyl)piperazin-1-yl]propylamine gave 2-{3-[4-(2-cyclopropylmethoxyphenyl)piperazin-1-yl]propylamino}-N,N-dimethylnicotinamide oxalate, m.p. 117°–123° C.; Anal.: Calcd. for $C_{25}H_{35}N_5O_2 \cdot C_2H_2O_4 \cdot (H_2O)_{0.65}$: C, 60.12; H, 7.16; N, 12.98%; Found: C, 60.13; H, 6.94; N, 12.82%;

substituting 3-{4-[2-(2-propynyloxy)phenyl]piperazin-1-yl}propylamine and recrystallizing from a solution of oxalic acid in alcohol gave 2-{3-[4-(2-(2-propynyloxy)phenyl)piperazin-1-yl]propylamino}-N,N-dimethylnicotinamide oxalate, m.p. 149°–150° C.; Anal.: Calcd. for $C_{24}H_{31}N_5O_2 \cdot C_2H_2O_4$: C, 61.04; H, 6.50; N, 13.69%; Found: C, 60.93; H, 6.61; N, 13.53%;

substituting {3-[4-(2-methoxyphenyl)piperazin-1-yl]propyl}(methyl) amine gave 2-({3-[4-(2-methoxyphenyl)piperazin-1-yl]propyl}(methyl)amino)-N,N-dimethylnicotinamide hydrochloride, m.p. 80° C. (dec); Anal.: Calcd. for $C_{23}H_{33}N_5O_2 \cdot (HCl)_3$: C, 53.02; H, 6.96; N, 13.44%; Found: C, 53.01; H, 7.32; N, 13.54%;

substituting 4-[4-(2-methoxyphenyl)piperazin-1-yl]-1-propanethiol gave 2-{3-[4-(2-methoxyphenyl) piperazin-1-yl]propylthio}-N,N-dimethylnicotinamide hydrochloride, m.p. 177°–182° C.; Anal.: Calcd. for $C_{25}H_{30}N_4O_2S \cdot (HCl)_3$: C, 50.43; H, 6.35; N, 10.69%; Found: C, 50.82; H, 6.65; N, 10.43%;

substituting 4-chloro-N,N-dimethylnicotinamide gave 4-{3-[4-(2-methoxyphenyl)piperazin-1-yl] propylamino}-N,N-dimethylnicotinamide hydrochloride, m.p. 172° C. (dec); Anal.: Calcd. for $C_{22}H_{31}N_5O_2 \cdot (HCl)_3 \cdot (H_2O)_{1.6}$: C, 49.32; H, 7.00; N, 13.07%; Found: C, 49.38; H, 6.83; N, 12.72%;

substituting N,N-diisopropyl-4-chloronicotinamide gave N,N-diisopropyl-4-{3-[4-(2-methoxyphenyl)piperazin-1-yl]propylamino}nicotinamide hydrochloride, m.p. 128°–136° C.; Anal.: Calcd. for $C_{26}H_{39}N_5O_2 \cdot (HCl)_{2.5}$: C, 57.32; H, 7.67; N, 12.85%; Found: C, 57.18; H, 7.56; N, 12.70%;

substituting 4-chloro-N,N-dimethyl-5-pyrimidinecarboxamide and recrystallizing from a solution of oxalic acid in alcohol gave 4-{3-[4-(2-methoxyphenyl)-piperazin-1-yl]propylamino}-N,N-dimethyl-5-pyrimidinecarboxamide oxalate, m.p. 103°–112° C.; Anal.: Calcd. for $C_{21}H_{30}N_6O_2 \cdot (C_2H_2O_4)_{0.3}$: C, 51.90; H, 6.09; N, 14.20%; Found: C, 51.36; H, 5.96; N, 13.84%;

substituting 3-[4-(2-fluorophenyl)piperazin-1-yl] propylamine gave 2-{3-[4-(2-fluorophenyl)piperazin- 1-yl]propylamino}-N,N-dimethylnicotinamide hydrochloride; Anal.: Calcd. for $C_{21}H_{28}FN_5O \cdot (HCl)_2 \cdot H_2O$: C, 52.94; H, 6.77; N, 14.70%; Found: C, 53.13%; H, 6.63; N, 14.54%;

substituting 3-[4-(2-cyclopropylphenyl)piperazin-1-yl] propylamine gave 2-{3-[4-(2-cyclopropylphenyl) piperazin-1-yl ]propylamino }-N,N-dimethylnicotinamide hydrochloride, m.p. 124°–133° C.; Anal.: Calcd. for $C_{24}H_{33}N_5O \cdot (HCl)_2 \cdot (H_2O)_{0.25}$: C, 59.68; H, 7.66; N, 14.20%; Found: C, 59.72; H, 7.43; N, 14.23%;

substituting 3-[4-(2-ethylphenyl)piperazin-1-yl] propylamine gave 2-{3-[4-(2-ethylphenyl)piperazin-1-yl]propylamino}-N,N-dimethylnicotinamide hydrochloride, m.p. 79°–81° C.; Anal.: Calcd. for $C_{23}H_{33}N_5O \cdot (HCl)_2 \cdot (H_2O)_{0.7}$: C, 57.42; H, 7.62; N, 14.55%; Found: C, 57.47; H, 7.49; N, 14.41%;

substituting 3-[4-(2,3-dimethylphenyl)piperazin-1-yl] propylamine gave N,N-dimethyl-2-{3-[4-(2,3-dimethylphenyl)piperazin-1-yl ]propylamino }nicotinamide hydrochloride, m.p. 94°–100° C.; Anal.: Calcd. for $C_{23}H_{30}N_5O \cdot HCl \cdot (H_2O)_{0.95}$: C, 61.50; H, 8.06; N, 15.59%; Found: C, 61.54; H, 7.66; N, 15.64%;

substituting 3-[4-(2-methylthiophenyl)piperazin-1-yl] propylamine gave N,N-dimethyl-2-{3-[4-(2-methylthiophenyl)piperazin-1-yl ]propylamino }nicotinamide hydrochloride, m.p. 137°–143° C.; Anal.: Calcd. for $C_{22}H_{31}SN_5O \cdot (HCl)_2 \cdot (C_4H_8O)_{0.1} \cdot (H_2O)_{0.4}$: C, 53.71; H, 6.96; N, 13.98%; Found: C, 53.79; H, 7.00; N, 13.98%;

substituting 3-[4-(2-cyanophenyl)piperazin-1-yl] propylamine gave 2-{3-[4-(2-cyanophenyl)piperazin-1-yl]propylamino}-N,N-dimethylnicotinamide hydrochloride, m.p. 129° C. (dec); Anal.: Calcd. for $C_{22}H_{28}N_6O \cdot (HCl)_3 \cdot (H_2O)_{1.3}$: C, 50.42; H, 6.60; N, 15.40%; Found: C, 50.64; H, 6.16; N, 15.44%; and substituting 3-[4-(2-oxazol -2-ylphenyl)piperazin-1-yl] propylamine gave 2-{3-[4-(2-oxazol-2-ylphenyl) piperazin-1-yl]propylamino}-N,N-dimethylnicotinamide hydrochloride, m.p. 102°–104° C.; Anal.: Calcd. for $C_{22}H_{30}N_6O_2 \cdot (HCl)_2 \cdot (H_2O)_{1.25} \cdot C_2H_6O$: C, 54.36; H, 6.56; N, 15.63; Found: C, 54.38; H, 6.64; N, 15.65%.

EXAMPLE 22

2-Amino-N,N,5-trimethylbenzamide

The following is the preparation of a compound of Formula 8 in which t is 1, $R^3$ is dimethylaminocarbonyl, $R^4$ is methyl at the 5-position and $R^{10}$ is amino.

A mixture of 5-methyl-2-nitrobenzoic acid (10 g, 55.2 mmol) and oxalyl chloride (6 mL, 68.8 mmol) in 100 mL of methylene chloride was stirred under argon at room temperature for 2 hours. The mixture was concentrated and the residue was co-evaporated twice with toluene. The residue was dissolved in 60 mL of dioxane and the solution was added dropwise to a mixture of aqueous dimethylamine (8.2 g, 40% w/w, 72.7 mmol) and sodium hydroxide (2.2 g, 55 mmol) in 20 mL of dioxane at 0° C. The mixture was stirred at room temperature for 1 hour and then poured into water. The mixture was extracted with ethyl acetate (2×150 mL), dried (Na$_2$SO$_4$), filtered and concentrated to give N,N,5-trimethyl-2-nitrobenzamide (11 g, 52.8 mmol).

A mixture of N,N,5-trimethyl-2-nitrobenzamide (11 g, 52.8 mmol) and 5% palladium on carbon (1 g) in 100 mL of ethanol was stirred under a hydrogen atmosphere for 18 hours. Additional 5% palladium on carbon (1 g) was added and the mixture was stirred for approximately 8 hours. The mixture was filtered and the filtrate was concentrated. The residue was purified on silica gel by flash chromatography eluting with 4% ethanol/methylene chloride to give 2-amino-N,N,5-trimethylbenzamide (8 g, 44.9 mmol), m.p. 98°–99° C.

Proceeding as in Example 22, but substituting different starting materials for 5-methyl-2-nitrobenzoic acid, the following compounds of Formula 8 were prepared:

substituting 5-chloro-2-nitrobenzoic acid gave 2-amino-5-chloro-N,N-dimethyl-benzamide, m.p. 97°–98° C.;

substituting 2-nitrobenzoic acid gave 2-amino-N,N-dimethylbenzamide, m.p. 53°–54° C.;

substituting 4,5-dimethoxy-2-nitrobenzoic acid gave 2-amino-4,5-dimethoxy-N,N-dimethylbenzamide, m.p. 94°–103° C.;

substituting 3-methyl-2-nitrobenzoic acid gave 2-amino-N,N,3-trimethyl-benzamide, m.p. 95°–96° C.; and substituting 3-methoxy-2-nitrobenzoic acid gave 2-amino-3-methoxy-N,N-dimethyl-benzamide as an oil.

EXAMPLE 23

2-Hydroxy-N,N-dimethylbenzamide

The following is the preparation of a compound of Formula 8 in which t is 0, $R^3$ is dimethylaminocarbonyl and $R^{10}$ is hydroxy.

A mixture of acetylsalicyloyl chloride (3.4 g, 17 mmol) in 120 mL of THF was added dropwise to 30 mL of 40% aqueous dimethylamine (66 mmol). The mixture was stirred at room temperature for 3 hours and then sodium hydroxide (4 g, 0.1 mmol) was added. The mixture was stirred at room temperature for approximately 60 hours and then poured into 20 mL of water, acidified with 1N hydrochloric acid and extracted with ethyl acetate. The extract was dried (Na$_2$SO$_4$) and concentrated. The residue was purified on silica gel by flash chromatography eluting with 6% methanol/methylene chloride to give 2-hydroxy-N,N-dimethylbenzamide (2.4 g, 14.53 mmol), m.p. 145°–152° C.

EXAMPLE 24

2-Mercapto-N,N-dimethylbenzamide

The following is the preparation of a compound of Formula 8 in which t is 0, $R^3$ is dimethylaminocarbonyl and $R^{10}$ is mercapto.

A mixture of 2,2'-dithiosalicyclic acid (6.1 g, 20 mmol) was suspended in 100 mL of methylene chloride and 2 drops of DMF and then oxalyl chloride (3.9 mL, 45 mmol) was added dropwise. The mixture was stirred for 30 minutes and then concentrated to dryness. The residue was co-evaporated twice with toluene and then dissolved in 30 mL of THF. The solution was added to a solution of dimethylamine (30 mL, 40% in water, 66 mmol) in 10 mL of THF. The mixture was stirred at room temperature for approximately 12 hours and then concentrated to dryness. The residue was partitioned between saturated sodium bicarbonate solution and ethyl acetate. The organic layer was separated, dried (NaSO$_4$) and concentrated to dryness. The residue was purified on silica gel by flash chromatography eluting with 4% methanol/methylene chloride to give N,N-dimethyl-N',N'-dimethyl-2, 2'-dithiosalicylamide (5.6 g, 15.53 mmol), m.p. 118°–122° C.

A mixture of N,N-dimethyl-N',N'-dimethyl-2,2'-dithiosalicylamide (4.1 g, 11.3 mmol) and sodium borohydride (4 g, 105.7 mmol) in 50 mL of ethanol was stirred at room temperature for approximately 12 hours. The mixture was concentrated to dryness to give to give 2-mercapto-N, N-dimethylbenzamide.

EXAMPLE 25

2-Trifluoroacetylamino-N,N-dimethylbenzamide

The following is the preparation of a compound of Formula 8 in which t is 0, $R^3$ is dimethylaminocarbonyl and $R^{10}$ is trifluoroacetylamino.

A mixture of dimethylamine (30 g, 270 mmol) and sodium hydroxide (7.2 g, 180 mmol) in 60 mL of dioxane was stirred and 2-nitrobenzoyl chloride (23.8 mL, 180 mmol) in 100 mL of dioxane was added dropwise. The mixture was stirred at room temperature for approximately 12 hours and then partitioned between 100 mL of saturated sodium bicarbonate solution and 150 mL of ethyl acetate. The aqueous layer was extracted with ethyl acetate (2×100 mL) and the combined ethyl acetate was washed with brine, dried ($Na_2SO_4$) and concentrated. The residue was purified on silica gel by flash chromatography eluting with 4% methanol/methylene chloride to give N,N-dimethyl-2-nitrobenzamide (20 g, 103 mmol), m.p. 74°–76° C.

A mixture of N,N-dimethyl-2-nitrobenzamide (4.76 g, 24.5 mmol) and 10% palladium on carbon (470 mg) in 100 mL of ethanol was stirred under hydrogen at atmospheric pressure for approximately 12 hours. The mixture was filtered and concentrated to dryness to give 2-amino-N,N-dimethylbenzamide (4 g, 24.2 mmol), m.p. 53°–54° C.

A solution of 2-amino-N,N-dimethylbenzamide (3.6 g, 21.8 mmol) in 50 mL of pyridine was cooled to 0° C. and trifluoroacetic anhydride (4.0 mL, 29 mmol) was added dropwise. The mixture was aged at 4° C. for approximately 60 hours and then concentrated to dryness. The residue was partitioned between saturated sodium bicarbonate solution and ethyl acetate. The ethyl acetate layer was separated and dried to give to give 2-trifluoroacetylamino-N,N-dimethylbenzamide.

Proceeding as in Example 25 but replacing 2-amino-N,N-dimethylbenzamide with 2-amino-3-methoxy-N,N,-dimethylbenzamide gave 2-trifluoroacetylamino-3-methoxy-N,N,-dimethylbenzamide.

EXAMPLE 26

2-{3-[4-(2-methoxyphenyl)piperazin-1-yl]propylamino}-N,N-dimethylbenzamide

The following is the preparation of a compound of Formula I in which and t are each 0, X is NH, Y and Z are each CH, $R^1$ is methoxy, $R^2$ is hydro and $R^3$ is dimethylaminocarbonyl.

A solution of 3-[4-(2-methoxyphenyl)piperazin-1-yl]-1-propanol (24 g, 95.87 mmol), prepared as in Example 10, in 25 mL of triethylamine and 300 mL of methylene chloride was cooled to approximately 0° C. and then methanesulfonyl chloride (8.8 mL) was added dropwise. The mixture was stirred at approximately 0° C. for 1 hour and then at room temperature for 0.5 hours. The mixture was poured into saturated sodium carbonate and stirred for 15 minutes. The organic phase was separated, washed with saturated sodium carbonate (2×150 mL), dried (MgSO₄) and concentrated to give 3-[4-(2-methoxyphenyl)piperazin-1-yl]propyl methanesulfonate (21 g, 63.63 mmol).

A mixture of 3-[4-(2-methoxyphenyl)piperazin-1-yl] propyl methanesulfonate (2 g, 6.06 mmol), 2-amino-N,N-dimethylbenzamide (1 g, 6.06 mmol), prepared as in Example 22, and potassium carbonate (2.1 g, 15 mmol) in 50 mL of acetonitrile was heated at reflux for 30 hours. The mixture was poured into water and extracted with ethyl acetate. The organic phase was dried ($K_2CO_3$) and concentrated. The residue was purified on silica gel by flash chromatography eluting with 6% methanol/methylene chloride to give 2-{3-[4-(2-methoxyphenyl)-piperazin-1-yl]propylamino}-N,N-dimethylbenzamide (1.5 g, 3.78 mmol).

A solution of 2-{3-[4-(2-methoxyphenyl)piperazin-1-yl]propylamino}-N,N-dimethylbenzamide (0.55 g, 1.39 mmol) in 2 mL of 5% methanol/methylene chloride was acidified with 1.4 mL of 1M hydrochloric acid in methanol and then ether was added to give a precipitate. The supernatant was decanted and the precipitate was washed with ether, collected and dried to give 2-{3-[4-(2-methoxyphenyl) piperazin-1-yl]propylamino}-N,N-dimethylbenzamide hydrochloride (0.56 g, 1.27 mmol), m.p. 74°–79° C. Anal.: Calcd. for $C_{23}H_{32}N_4O_2 \cdot HCl \cdot (H_2O)_{0.5}$: C, 62.50; H, 7.75; N, 12.68%; Found: C, 62.27; H, 7.85; N, 13.02%.

Proceeding as in Example 26, but substituting different starting materials for 3-[4-(2-methoxyphenyl)piperazin-1-yl]-1-propanol, methanesulfonyl chloride and/or 2-amino-N,N-dimethylbenzamide the following compounds of Formula I were prepared:

substituting 3-[4-(2-nitrophenyl)piperazin-1-yl]-1-propanol and 2-amino-N,N, 5-trimethylbenzamide gave 2-{3-[4-(2-nitrophenyl)piperazin-1-yl]propylamino}-N,N,5-trimethylbenzamide hydrochloride, m.p. 198°–200° C.; Anal.: Calcd. for $C_{23}H_{31}N_5O_3 \cdot (HCl)_2$: C, 55.42; H, 6.47; N, 14.05%; Found: C, 55.11; H, 6.71; N, 13.93%;

substituting 2-amino-N,N,5-trimethylbenzamide gave 2-{3-[4-(2-methoxyphenyl)-piperazin-1-yl]propylamino}-N,N,5-trimethylbenzamide hydrochloride; Anal.: Calcd. for $C_{24}H_{34}N_4O_2 \cdot (HCl) \cdot (H_2O)_{1.5}$: C, 60.81; H, 8.08; N, 11.82%; Found: C, 60.99; H, 7.70; N, 11.77%;

substituting 2-amino-N,N,6-trimethylbenzamide gave 2-{3-[4-(2-methoxyphenyl)piperazin-1-yl] propylamino}-N,N,6-trimethylbenzamide hydrochloride, m.p. 66°–70° C.; Anal.: Calcd. for $C_{24}H_{34}N_4O_2 \cdot (HCl)_2 \cdot (H_2O)$: C, 62.12; H, 7.82; N, 12.08%; Found: C, 61.82; H, 7.62; N, 11.81%;

substituting 2-aminoacetophenone gave 2-{3-[4-(2-methoxyphenyl)-piperazin-1-yl] propylamino}acetophenone hydrochloride, m.p. 172°–181° C.; Anal.: Calcd. for $C_{22}H_{29}N_3O_2 \cdot HCl \cdot H_2O$: C, 62.62; H, 7.64; N, 9.965%; Found: C, 62.65; H, 7.49; N, 10.23%;

substituting 2-mercapto-N,N-dimethylbenzamide gave 2-{3-[4-(2-methoxyphenyl)piperazin-1-yl] propylthio}-N,N-dimethylbenzamide hydrochloride, m.p. 174°–177° C.; Anal.: Calcd. for $C_{23}H_{31}SN_3O_{HCl.H2}O$: C, 59.03; H, 7.32; N, 8.98%; Found: C, 58.95; H, 6.93; N, 9.00%; and substituting 2-hydroxy-N,N-dimethylbenzamide gave 2-{3-[4-(2-methoxyphenyl)piperazin-1-yl]propoxy}-N,N-dimethylbenzamide hydrochloride, m.p. 160°–162° C.; Anal.: Calcd. for $C_{23}H_{31}ON_3O_2 \cdot (HCl)_2$: C, 58.72; H, 7.07; N, 8.93%; Found: C, 58.54; H, 6.96; N, 8.72%.

Proceeding as in Example 26, but reacting 1-chloro-3-[4-(2-methoxyphenyl)-piperazin-1-yl]propane with 2-amino-5- chloro-N,N-dimethylbenzamide gave 5-chloro-2-{3-[4-(2-methoxyphenyl)piperazin-1-yl]propylamino}-N,N-dimethylbenzamide hydrochloride, m.p. 100°–108° C.; Anal.: Calcd. for $C_{23}H_{31}ClN_4O_2 \cdot (HCl)_2 \cdot (H_2O)_{0.75}$: C, 57.38; H, 7.02; N, 11.65%; Found: C, 57.47; H, 6.94; N, 11.48%;

EXAMPLE 27

2-{3-[4-(2-Methoxyphenyl)piperazin-1-yl]propylamino}-N,N,3-trimethylbenzamide

The following is the preparation of a compound of Formula I in which p is 0, t is 1, X is NH, Y and Z are each CH, $R^1$ is methoxy, $R^2$ is hydro, $R^3$ is dimethylaminocarbonyl and $R^4$ is methyl at the 3-position.

A mixture of 2-trifluoroacetylamino-N,N,3-trimethylbenzamide (584.2 mg, 2.13 mmol), prepared as in Example 22, and sodium hydride (110 mg, 2.7 mmol) in 10 mL of DMF was heated at 50° C. for 20 minutes and then 1-chloro-3-[4-(2-methoxyphenyl)piperazin-1-yl]propane (647 mg, 2.13 mmol) was added. The mixture was heated at 80° C. for 18 hours, then poured into water and extracted with ethyl acetate (3×50 mL). The combined extract was washed with saline, dried (MgSO$_4$) and concentrated. The residue was purified on silica gel by column chromatography eluting with 6% methanol/methylene chloride to give 2-{3-[4-(2-methoxy-phenyl)piperazin-1-yl]propylamino}-N,N,3-trimethylbenzamide (100 mg, 0.24 mmol).

A solution of 2-{3-[4-(2-methoxyphenyl)piperazin-1-yl]propylamino}-N,N,3-trimethylbenzamide (70 mg, 0.17 mmol) in 0.5 mL of 5% methanol/methylene chloride was acidified with 0.6 mL of 1M hydrochloric acid in methanol and then ethyl acetate was added to give a precipitate. The supernatant was decanted and the precipitate was washed with ether, collected and dried to give 2-{3-[4-(2-methoxyphenyl)piperazin-1-yl]propylamino}-N,N,3-trimethylbenzamide hydrochloride (75 mg, 0.15 mmol). Anal.: Calcd. for $C_{24}H_{34}N_4O_2 \cdot (HCl)_2 \cdot (H_2O)_{0.5}$: C, 58.53; H, 7.57; N, 11.38%; Found: C, 58.52; H, 7.68; N, 10.99%.

Proceeding as in Example 27, but substituting 2-trifluoroacetylamino-3-methoxy-N,N-dimethylbenzamide for 2-trifluoroacetylamino-N,N,3-trimethyl-benzamide, gave 3-methoxy-2-{3-[4-(2-methoxyphenyl)piperazin-1-yl]propylamino}-N,N-dimethylbenzamide hydrochloride, m.p. 108°–109° C.; Anal.: Calcd. for $C_{24}H_{34}N_4O_3 \cdot (HCl)_2 \cdot (H_2O)_{1.25}$: C, 55.22; H, 7.43; N, 10.73%; Found: C, 55.0; H, 7.71; N, 10.34%.

EXAMPLE 28

2-(3-Chloropropyl)amino-N,N-dimethylbenzamide

The following is the preparation of a compound of Formula 9 in which t is 0, L is chloro, X is NH and $R^3$ is dimethylaminocarbonyl.

A mixture of 2-amino-N,N-dimethylbenzamide (1.15 g, 6.97 mmol), prepared as in Example 22, potassium carbonate (1.44 g, 10.46 mmol) and 1-bromo-3-chloro-propane (0.7 mL, 7 mmol) in 10 mL of DMF was stirred at room temperature for 16 hours and then at 70° C. for an additional 4 hours. The mixture was poured into water and extracted with ethyl acetate (3×20 mL). The combined extract was washed with brine, dried (MgSO$_4$) and concentrated to give 2-(3-chloropropyl)amino-N,N-dimethylbenzamide as a crude mixture.

Proceeding as in Example 28, but substituting different starting materials for 2-amino-N,N-dimethylbenzamide the following compounds of Formula 13 were prepared: substituting 2-amino-4,5-dimethoxy-N,N-dimethylbenzamide gave 2-(3-chloro-propyl)amino-4,5-dimethoxy-N,N-dimethylbenzamide as a crude mixture;

substituting methanesulfonyl chloride gave 2-(3-mesyloxypropyl)amino-N,N-dimethylbenzamide as a crude mixture; and substituting 2-amino-N,N,5-trimethylbenzamide and methanesulfonyl chloride gave 2-(3-mesyloxypropyl)amino-N,N,5-trimethylbenzamide as a crude mixture.

EXAMPLE 29

2-{3-[4-(5-Chloro-2-methoxyphenyl)piperazin-1-yl]propylamino}-N,N-dimethylbenzamide The following is the preparation of a compound of Formula I in which p and t are each 0, X is NH, Y and Z are each CH, $R^1$ is methoxy, $R^2$ is chloro at the 5-position and $R^3$ is dimethylaminocarbonyl.

A mixture of 1-(5-chloro-2-methoxyphenyl)piperazine (365 mg, 1.6 mmol), prepared as in Example 2, 2-(3-chloropropyl)amino-N,N-dimethylbenzamide (385 mg of crude mixture), prepared as in Example 28, potassium carbonate (550 mg, 3.98 mmol) and sodium iodide (240 mg, 1.6 mmol) in 20 mL of acetonitrile was heated at reflux for 18 hours. The mixture was poured into water and extracted with ethyl acetate (2×50 mL). The combined extract was washed with brine, dried (MgSO$_4$) and concentrated. The residue was purified on silica gel by flash chromatography eluting with 6% methanol/methylene chloride to give 2-{3-[4-(5-chloro-2-methoxyphenyl)piperazin-1-yl]propylamino}-N,N-dimethylbenzamide (280 mg, 0.65 mmol).

A solution of 2-{3-[4-(5-chloro-2-methoxyphenyl)piperazin-1-yl]propyl-amino}-N,N-dimethylbenzamide (265 mg, 0.61 mmol) in 0.4 mL of 5% methanol/methylene chloride was acidified with 2 mL of 1M hydrochloric acid in methanol and then ether was added to give a precipitate. The supernatant was decanted and the precipitate was washed with ether, collected and dried to give 2-{3-[4-(5-chloro-2-methoxyphenyl)-piperazin-1-yl]propylamino}-N,N-dimethylbenzamide hydrochloride (270 mg, 0.57 mmol), m.p. 90°–135° C. Anal.: Calcd. for $C_{23}H_{31}ClN_4O_2 \cdot HCl \cdot (H_2O)_{0.5}$: C, 57.98; H, 6.98; N, 11.76%; Found: C, 57.79H, 6.80; N, 11.72%.

Proceeding as in Example 29, but substituting different starting materials for 3-[4-(5-chloro-2-methoxyphenyl)piperazine and/or 2-(3-chloropropyl)amino-N,N-dimethylbenzamide, the following compounds of Formula I were prepared:

substituting 1-[2-(2,2,2-trifluoroethoxy)phenyl]piperazine and 2-(3-mesyloxypropyl)amino-5-cyano-N,N,-dimethylbenzamide gave 2-(3-{4-[2-(2,2,2-trifluoroethoxy)phenyl]piperazin-1-yl}propylamino)-N,N-dimethylbenzamide hydrochloride, m.p. 161°–170° C.; Anal.: Calcd. for $C_{25}H_{30}F_3N_5O_2 \cdot HCl \cdot H_2O$: C, 55.19; H, 6.11; N, 12.88%; Found: C, 54.99H, 6.04; N, 12.65%;

substituting 1-(2-methoxyphenyl)piperazine and 2-(3-chloropropyl)amino-4,5-dimethoxy-N,N-dimethylbenzamide gave 4,5-dimethoxy-2-{3-[4-(2-methoxyphenyl)piperazin-1-yl]propylamino}-N,N,-dimethylbenzamide hydrochloride, m.p. 79°–82° C.; Anal.: Calcd. for $C_{25}H_{36}N_4O_4 \cdot HCl \cdot (H_2O)_{0.25}$: C, 60.35; H, 7.60; N, 11.26%; Found: C, 60.18H, 7.75; N, 11.35%;

substituting 1-(4-fluoro-2-methoxyphenyl)piperazine hydrochloride gave 2-{3-[4-(4-fluoro-2-methoxyphenyl)piperazin-1-yl]propylamino}-N,N-dimethylbenzamide hydrochloride, m.p. 208°–210° C.; Anal.: Calcd. for $C_{23}H_{31}FN_4O_2 \cdot HCl \cdot (H_2O)_{0.2}$: C, 60.77; H, 7.18; N, 12.33%; Found: C, 60.63H, 7.12; N, 12.26%;

substituting 1-(4-fluoro-2-methoxyphenyl)piperazine and 2-(3-mesyloxypropyl)amino-N,N,5-trimethylbenzamide gave 2-{3-[4-(4-fluoro-2-methoxyphenyl)piperazin-1-yl]propylamino}-N,N,5-trimethylbenzamide hydrochloride, m.p. 99°–115° C.; Anal.: Calcd. for $C_{24}H_{33}FN_4O_2 \cdot HCl \cdot H_2O$: C, 59.64; H, 7.51; N, 11.60%; Found: C, 59.76H, 7.16; N, 11.63%;

substituting 1-(5-fluoro-2-methoxyphenyl)piperazine and 2-(3-mesyloxypropyl)amino-N,N,5,-trimethylbenzamide gave 2-{3-[4-(5-fluoro-2-methoxyphenyl)piperazin-1-yl]propylamino}-N,N,5-trimethylbenzamide hydrochloride; Anal.: Calcd. for $C_{24}H_{33}FN_4O_2 \cdot HCl \cdot (H_2O)_{0.75}$: C, 60.24; H, 7.48; N, 11.71%; Found: C, 60.17H, 7.24; N, 11.62%;

substituting 1-(5-fluoro-2-methoxyphenyl)piperazine gave 2-{3-[4-(5-fluoro-2-methoxyphenyl)piperazin-1-yl]-propylamino}-N,N-dimethylbenzamide hydrochloride, m.p. 82°–93° C.; Anal.: Calcd. for $C_{23}H_{31}FN_4O_2 \cdot HCl \cdot (H_2O)_{0.5}$: C, 60.05; H, 7.23; N, 12.18%; Found: C, 59.68H, 7.12; N, 11.97%;

substituting 1-[2-(2,2,2-trifluoroethoxy)phenyl]piperazine and 2-(3-mesyloxypropyl)amino-N,N,5-trimethylbenzamide gave 2-(3-{4-[2-(2,2,2-trifluoroethoxy)phenyl]piperazin-1-yl}propylamino)-N,N,5-trimethylbenzamide hydrochloride, m.p. 58°–65° C.; Anal.: Calcd. for $C_{25}H_{33}F_3N_4O_2 \cdot HCl \cdot (H_2O)_{1.5}$: C, 55.40; H, 6.88; N, 10.34%; Found: C, 55.20H, 6.54; N, 10.36%; and substituting 1-[2-(2,2,2-trifluoroethoxy)phenyl]piperazine and 2-(3-mesyloxypropyl)amino-N,N-dimethylbenzamide gave 2-(3-{4-[2-(2,2,2-trifluoroethoxy)phenyl]piperazin-1-yl}propylamino)-N,N-dimethylbenzamide hydrochloride, m.p. 73°–109° C.; Anal.: Calcd. for $C_{24}H_{31}F_3N_4O_2 \cdot HCl \cdot H_2O$: C, 55.54; H, 6.60; N, 10.80%; Found: C, 55.54H, 6.30; N, 10.81%.

EXAMPLE 30

2-{3-[4-(2-methoxyphenyl)-1-methylpiperazin-1-yl]propylamino}-N,N-dimethylnicotinamide iodide The following is the preparation of a compound of Formula I in which p is 1, t is 0, X is NH, Y is N, Z is CH, $R^1$ is methoxy, $R^2$ is hydro, $R^3$ is dimethylaminocarbonyl and $R^5$ is methyl.

A mixture of 2-{3-[4-(2-methoxyphenyl)piperazin-1-yl]propylamino}-N,N-dimethylnicotinamide (256 mg, 0.64 mmol), prepared as in Example 21, and iodomethane (0.05 mL, 0.83 mmol) in 8 mL of ethanol was stirred at room temperature for approximately 12 hours. Additional iodomethane (0.05 mL, 0.83 mmol) was added and the mixture was stirred at room temperature for approximately 14 hours. Additional iodomethane (0.04 mL, 0.64 mmol) was added and the mixture was stirred for approximately 4 hours. The mixture was basified with aqueous potassium carbonate and then extracted with methylene chloride. The extract was washed with brine and concentrated. The residue then was triturated with diethyl ether. The diethyl ether was removed by evaporation and the residue was dissolved in ethyl acetate and treated with excess hydrochloric acid in methanol and concentrated to dryness. The residue was recrystallized from methylene chloride and the crystals were triturated with diethyl ether several times and dried to give 2-{3-[4-(2-methoxyphenyl)-1-methyl-piperazin-1-yl]propylamino}-N,N-dimethylnicotinamide iodide hydrochloride (120 mg, 0.21 mmol). Anal.: Calcd. for $C_{23}H_{34}IN_5O_2 \cdot HCl$: C, 47.96; H, 6.12; N, 12.12%; Found: C, 47.19H, 6.68; N, 10.80%.

Proceeding as in Example 30, but replacing 2-{3-[4-(2-methoxyphenyl)-piperazin-1-yl]propylamino}-N,N-dimethylnicotinamide with 2-({3-[4-(2-methoxy-phenyl)piperazin-1-yl]propyl}(methyl)amino)-N,N-dimethylbenzamide gave 2-({3-[4-(2-methoxyphenyl)-1-methylpiperazin-1-yl]propyl}(methyl)amino)-N,N-dimethylbenzamide iodide, m.p. 77°–83° C.; Anal.: Calcd. for $C_{25}H_{37}IN_4O_2$: C, 54.35; H, 6.75; N, 10.14%; Found: C, 54.36H, 6.69; N, 10.50%.

EXAMPLE 31

2-({3-[4-(2-methoxyphenyl)-1-methylpiperazin-1-yl]propyl}(methyl)amino)-N,N-dimethylbenzamide iodide The following is the preparation of a compound of Formula I in which p is 1, t is 0, X is $N(CH_3)$, Y and Z are each CH, $R^1$ is methoxy, $R^2$ is hydro, $R^3$ is dimethylaminocarbonyl and $R^5$ is methyl.

A mixture of 2-{3-[4-(2-methoxyphenyl)piperazin-1-yl]propylamino}-N,N-dimethylbenzamide (270 mg, 0.68 mmol), prepared as in Example 26, and sodium hydride (35 mg, 60%, 0.88 mmol) in 2 mL of DMF was heated at 50° C. for 15 minutes and than iodomethane (0.125 mL, 2 mmol) was added. The mixture was stirred at 50° C. for 17 hours, poured into 10 mL of water and extracted with ethyl acetate (2×50 mL). The combined extract was washed with brine, dried ($K_2CO_3$) and concentrated. The residue recrystallized from methylene chloride to give 2-({3-[4-(2-methoxyphenyl)-1-methylpiperazin-1-yl]propyl}(methyl)amino)-N,N-dimethylbenzamide iodide (224.1 mg, 0.41 mmol), m.p. 77°–82° C. Anal.: Calcd. for $C_{25}H_{37}IN_4O_2$: C, 54.35; H, 6.75; N, 10.14%; Found: C, 54.38H, 6.69; N, 10.50%.

EXAMPLE 32

2-{3-[4-(2-Hydroxyphenyl)piperazin-1-yl]propylamino}-N,N-dimethylnicotinamide

The following is the preparation of a compound of Formula I in which p and t are each 0, X is NH, Y is N, Z is CH, $R^1$ is hydroxy, $R^2$ is hydro and $R^3$ is dimethylaminocarbonyl.

A mixture of 2-{3-[4-(2-methoxyphenyl)piperazin-1-yl]propylamino}-N,N-dimethylnicotinamide (0.54 g, 1.36 mmol), prepared as in Example 21, and sodium cyanide (0.33 g, 6.8 mmol) in 12 mL of DMSO was heated at reflux for 14 hours and then diluted with water and extracted twice with diethyl ether. The aqueous layer was extracted twice with methylene chloride and the combined methylene chloride layers were washed with water and brine, dried ($MgSO_4$), filtered and concentrated. The residue was purified on silica gel by column chromatography eluting with 8% methanol/methylene chloride to give 2-{3-[4-(2-hydroxyphenyl)-piperazin-1-yl]propylamino}-N,N-dimethylnicotinamide (0.134 g, 0.35 mmol) as an oil. The free base was recrystallized from a solution of fumaric acid in alcohol to give di(2-{3-[4-(2-hydroxyphenyl)-piperazin-1-yl]propylamino}-N,N-dimethylnicotinamide) fumarate, m.p. 185°–186° C. Anal.: Calcd. for $C_{21}H_{30}N_5O_2 \cdot (C_4H_4O_4)_{0.5}$: C, 62.57; H, 7.08; N, 15.86; Found: C, 62.44H, 7.08; N, 15.73%.

EXAMPLE 33

5-Chloro-2-{3-[4-(2-methoxyphenyl)piperazin-1-yl]propylamino}-N,N-dimethylnicotinamide The following is the preparation of a compound of Formula I in which p is 0, t is 1, X is NH, Y is N, Z is CH, $R^1$ is methoxy, $R^2$ is hydro, $R^3$ is dimethylaminocarbonyl and $R^4$ is chloro at the 5-position.

A mixture of 2-{3-[4-(2-methoxyphenyl)piperazin-1-yl]propylamino}-N,N-dimethylnicotinamide hydrochloride (0.287 g, 0.66 mmol), prepared as in Example 21, in 6 mL of DMF was heated to 50° C. and N-chlorosuccinimide (0.1 g, 0.73 mmol) was added. The mixture was stirred at 55° C. for 4 hours, diluted with water and basified with $K_2CO_3$ giving a precipitate. The precipitate was extracted with diethyl ether and the ether layer was washed twice with brine, dried (MgSO₄) and concentrated. The residue was purified on silica gel by column chromatography eluting with 5% methanol/methylene chloride to give 5-chloro-2-{3-[4-(2-methoxyphenyl)piperazin-1-yl]propylamino}-N,N-dimethylnicotinamide (0.188 g, 0.435 mmol) as an oil.

The 5-chloro-2-{3-[4-(2-methoxyphenyl)piperazin-1-yl]propylamino}-N,N-dimethylnicotinamide (0.188 g, 0.435 mmol) was dissolved in methylene chloride and the solution was treated with excess hydrochloric acid in methanol and concentrated to dryness. The residue was triturated with diethyl ether and then dried to give 5-chloro-2-{3-[4-(2-methoxyphenyl)piperazin-1-yl]propyl-amino}-N,N-dimethylnicotinamide hydrochloride (0.18 g, 0.33 mmol), Anal.: Calcd. for $C_{22}H_{30}ClN_5O_2 \cdot (HCl)_3 \cdot (C_4H_8O)_{0.3}$: C, 49.08; H, 6.28; N, 12.33%; Found: C, 48.70H, 6.46; N, 11.93%.

Proceeding as in Example 33, but substituting 2-{3-[4-(4-fluoro-2-methoxyphenyl)piperazin-1-yl]propylamino}-N,N-dimethylnicotinamide hydrochloride for 2-{3-[4-(2-methoxyphenyl)piperazin-1-yl]propylamino}-N,N-dimethylnicotinamide hydrochloride, gave 5-chloro-2-{3-[4-(4-fluoro-2-methoxyphenyl)piperazin-1-yl]propylamino}-N,N-dimethylnicotinamide hydrochloride, m.p. 223°–224° C. Anal.: Calcd. for $C_{22}H_{29}FClN_5O_2 \cdot HCl$: C, 54.32; H, 6.21; N, 14.39%; Found: C, 54.18; H, 6.20; N, 14.19%.

EXAMPLE 34

2-{3-[4-(4-Bromo-2-methoxyphenyl)piperazin-1-yl]propylamino}-N,N-dimethylnicotinamide The following is the preparation of a compound of Formula I in which p and t are each 0, X is NH, Y is N, Z is CH, $R^1$ is methoxy, $R^2$ is bromo at the 4-position and $R^3$ is dimethylaminocarbonyl.

2-{3-[4-(2-Methoxyphenyl)piperazin-1-yl]propylamino}-N,N-dimethylnicotinamide (0.21 g, 0.53 mmol), prepared as in Example 21, was dissolved in methylene chloride and the solution was treated with excess hydrochloric acid in methanol and concentrated under reduced pressure. The residue was dissolved in 6 mL of DMF and N-bromosuccinimide (0.101 g, 0.57 mmol) was added. The mixture was stirred at room temperature for approximately 24 hours, diluted with water and basified with $K_2CO_3$. The basified mixture was extracted with ethyl acetate and the ethyl acetate layer was washed with brine, dried (MgSO₄), filtered and concentrated. The residue was purified on silica gel by column chromatography eluting with 5% methanol/methylene chloride to give 2-{3-[4-(4-bromo-2-methoxyphenyl)piperazin-1-yl]propylamino}-N,N-dimethylnicotinamide (0.19 g, 0.40 mmol) as an oil.

The 2-{3-[4-(4-bromo-2-methoxyphenyl)piperazin-1-yl]propylamino}-N,N-dimethylnicotinamide (0.19 g, 0.40 mmol) was dissolved in methylene chloride and the solution was treated with excess hydrochloric acid in methanol and concentrated to dryness. The residue was triturated with ethyl acetate and dried to give 2-{3-[4-(4-bromo-2-methoxyphenyl)piperazin-1-yl]propylamino}-N,N-dimethylnicotinamide hydrochloride. Anal.: Calcd. for $C_{22}H_{30}BrN_5O_2 \cdot (HCl)_2 \cdot H_2O$: C, 46.96; H, 6.37; N, 11.60%; Found: C, 46.56H, 6.37; N, 11.60%.

EXAMPLE 35

2-{3-[4-(4-Cyano-2-methoxyphenyl)piperazin-1-yl]propylamino}-N,N-dimethylnicotinamide The following is the preparation of a compound of Formula I in which t are each 0, X is NH, Y is N, Z is CH, $R^5$ is methoxy, $R^2$ is cyano at the 4-position and $R^3$ is dimethylaminocarbonyl.

A mixture of 2-{3-[4-(4-bromo-2-methoxyphenyl)piperazin-1-yl]propylamino}-N,N -dimethylnicotinamide (240 mg, 0.5 mmol), prepared as in Example 34, and copper(I) cyanide (60 mg, 0.66 mmol) in 2 mL of anhydrous NMP was heated at 200° C. under a nitrogen atmosphere for 20 hours. The mixture was concentrated and the residue was combined with a water/ammonium mixture. The mixture was extracted with methylene chloride and the methylene chloride layer was washed with brine, dried (MgSO₄), filtered and concentrated. The residue was dissolved in acetonitrile and the solution was treated with excess hydrochloric acid in methanol and concentrated. The residue was crystallized from 10% acetonitrile/ethyl acetate to give 2-{3-[4-(4-cyano-2-methoxyphenyl)-piperazin-1-yl]propylamino}-N,N-dimethylnicotinamide hydrochloride (45 mg, 0.11 mmol), m.p. 61°–64° C. Anal.: Calcd. for $C_{23}H_{30}N_6O_2 \cdot (HCl)_2 \cdot C_4H_8O \cdot (H_2O)_{1.2}$: C, 55.76; H, 6.51; N, 16.96%; Found: C, 53.66H, 6.78; N, 15.50%.

EXAMPLE 36

2-{3-[4-(2-aminophenyl)piperazin-1-yl]propylamino}-N,N,5-trimethylbenzamide

The following is the preparation of a compound of Formula I in which p is 0, t is 1, X is NH, Y and Z are each CH, $R^1$ is amino, $R^2$ is hydro, $R^3$ is dimethylaminocarbonyl and $R^4$ is methyl at the 5-position.

A mixture of 2-{3-[4-(2-nitrophenyl)piperazin-1-yl]propylamino}-N,N,5-trimethylbenzamide (580 mg, 1.36 mmol), prepared as in Example 26, and 10% palladium on carbon (70 mg) in 15 mL of ethanol was added and stirred under hydrogen at room temperature for approximately 12 hours. The mixture was filtered and concentrated to give 2-{3-[4-(2-aminophenyl)piperazin-1-yl]propyl-amino}-N,N,5-trimethylbenzamide.

EXAMPLE 37

2-{3-[4-(2-acetylaminophenyl)piperazin-1-yl]propylamino}-N,N,5-trimethylbenzamide The following is the preparation of a compound of Formula I in which p is 0, t is 1, X is NH, Y and Z are each CH, $R^1$ is acetylamino, $R^2$ is hydro, $R^3$ is dimethylaminocarbonyl and $R^4$ is methyl at the 5-position.

A solution of 2-{3-[4-(2-aminophenyl)piperazin-1-yl]propylamino}-N,N,5-trimethylbenzamide (398 mg, 1.01 mmol), prepared as in Example 36, in 10 mL of pyridine was cooled to 0° C. and methanesulfonyl chloride (0.08 mL, 1.03 mmol) was added slowly. The mixture was stirred at 0° C. for 2 hours and then evaporated to dryness. The residue was partioned between saturated sodium bicarbonate and ethyl acetate. The organic layer was separated, dried ($K_2CO_3$) and evaporated to dryness. The residue was purified on silica gel by column chromatography eluting with 5% methanol/methylene chloride to give 2-{3-[4-(2-methylsulfonylaminophenyl)-piperazin-1-yl]propylamino}-N,N,5-trimethylbenzamide hydrochloride, m.p. 207°–209° C.; Anal.: Calcd. for $C_{24}H_{35}N_5O_3S.(HCl)_2.(H_2O)_{0.5}$: C, 51.89; H, 6.90; N, 12.61%; Found: C, 51.9; H, 6.74.; N, 12.56%.

Proceeding as in Example 37, but substituting different starting materials for acetic anhydride, the following compounds Formula I were prepared:

substituting trifluoroacetic anhydride gave 2-{3-[4-(2-trifluoroacetylaminophenyl)piperazin-1-yl]propylamino}-5N,N,5-trimethylbenzamide hydrochloride; Anal.: Calcd. for $C_{25}H_{32}F_3N_5O_2.(HCl)_2$: C, 53.19; H, 6.07; N, 12.41%; Found: C, 53.44; H, 6.31; N, 12.20%; and substituting acetic anhydride gave 2-{3-[4-(2-acetylaminophenyl)piperazin-1-yl]propylamino}-N,N,5-trimethylbenzamide hydrochloride, m.p. 113°–142° C.; Anal.: Calcd. for $C_{25}H_{35}N_5O_2.HCl(H_2O)_{0.5}$: C, 62.16; H, 7.72; N, 14.50%; Found: C, 61.77; H, 7.70; N, 14.39%.

EXAMPLE 38

The following are representative pharmaceutical formulations containing a compound of Formula I.

| ORAL FORMULATION |  |
| --- | --- |
| A representative solution for oral administration contains: | |
| Compound of Formula I | 100–1000 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| A representative solution for intravenous administration contains: | |
| Compound of Formula I | 10–100 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| A representative tablet form of a compound of Formula I may contain: | |
| Compound of Formula I | 1% |
| Microcrystalline Cellulose | 73% |
| Stearic Acid | 25% |
| Colloidal Silica | 1% |

EXAMPLE 39

$\alpha_1$-Adrenoceptor In Vitro, Functional Assay in Tissue Isolated from Rabbit and Rat The following describes in vitro assays for measuring the relative effect of test compounds on $\alpha_1$-adrenoceptor mediated contraction of rat, isolated aortic smooth muscle and rabbit, isolated urinary bladder smooth muscle.

Thoracic aorta were isolated from rats and immediately immersed in Krebs' solution (comprising in mM concentrations: NaCl, 118.5; $NaHCO_3$, 25; dextrose, 5; KCl, 4.8; $CaCl_2$, 2.5; $MgSO_4$, 1.2; $KH_2PO_4$, 1.2; cocaine, 0.03; corticosterone, 0.03; propranolol, 0.001; ascorbic acid, 0.1; and indomethacin, 0.01). The aortas were dissected free from extraneous tissue and then a cross sectional ring approximately 3 mm in length was cut from the most proximal segment. The aortic rings were suspended vertically in 10 mL tissue baths and bathed in Kreb's solution maintained at 37° C. and constantly aerated with a 95% $O_2$ and 5% $CO_2$ gas mixture. A resting tension of 1 g was applied to each aortic ring and thereafter periodically readjusted to maintain a 1 g resting tension throughout the duration of the assay.

Urinary bladders were emptied and isolated from rabbits. Bladders were dissected free from extraneous tissue and then a cross sectional ring of bladder neck tissue was cut above the urethra to approximately one third of the way up the bladder. The bladder neck was cut parallel to the longitudinal muscle fibers to give flat section of muscle tissue and then the flat section was cut parallel to the longitudinal muscle to give several flat strips. Strips of bladder tissue were suspended vertically in 10 mL tissue baths and bathed in Kreb's solution maintained at 33° C. and constantly aerated with a 95% $O_2$ and 5% $CO_2$ gas mixture. A resting tension of 5 g was applied to each urinary bladder strip. The strips were allowed to relax to a resting tension of 1 g and thereafter periodically readjusted to maintain the 1 g resting tension throughout the duration of the assay.

The aortic ring or urinary bladder strip preparations were allowed to equilibrate for 60 minutes during which period the bath solution was replaced every 15 minutes. The tissue was then exposed to bath solution containing norepinephrine (0.1 to 10 µM) and once a steady state contraction was produced the tissue was exposed to bath solution free of norepinephrine, replacing the solution twice every 5 minutes for 30 minutes. The aortic rings were exposed to norepinephrine and the urinary bladder strips to phenylephrine in a cumulative concentration fashion. That is, the isolated tissue was exposed to bath solution containing a threshold concentration of either norepinephrine or phenylephrine until a steady state contractile response was attained and then the concentration of agonist was cumulatively increased by 0.5 log increments until a maximal or near maximal response was attained. Norepinephrine produced a concentration-dependent, $\alpha_1$-adrenoceptor mediated contraction of the aortic rings. Phenylephrine produced a concentration-dependent, $\alpha_1$-adrenoceptor mediated contraction of the urinary bladder strips.

The tissue was then exposed to solution free of agonist, replacing the solution twice every 5 minutes for 30 minutes. After baseline tension was established and readjusted to 1 g, the tissue was exposed to bath solution containing the test compound, replacing the solution every 15 minutes for 60 minutes. In the presence of the test compound, the tissue again was exposed to either norepinephrine or phenylephrine in a cumulative concentration fashion, increasing the agonist concentration until a maximal or near maximal response was achieved.

The concentration ratio (CR) of agonist necessary to produce equiactive responses in the absence and presence of the test compound was determined. Relying on the concentration ratio, the assay concentration (molar) of the test compound, and the relationship:

$$pA_2 = -\log \frac{[\text{test compound}]}{CR - 1}$$

the negative log of the dissociation constant ($pA_2$) for each test compound at $\alpha_1$-adrenoceptors were estimated for both aortic tissue and urinary bladder tissue.

Proceeding as in Example 39, compounds of Formula I were tested and found to selectively inhibit the $\alpha_1$-adrenoceptor mediated contractions of rabbit, isolated urinary bladder smooth muscle. In contrast, prazosin, an $\alpha_1$-adrenoceptor antagonist that has been proscribed for treating BPH, selectively inhibited the $\alpha_1$-adrenoceptor mediated contractions of rat, isolated aortic smooth muscle.

EXAMPLE 40

$\alpha_1$-Adrenoceptor In Vitro, Functional Assay in Tissue Isolated from Human The following describes in vitro assays for measuring the relative effect of test compounds on $\alpha_1$-adrenoceptor mediated contractions of human, isolated arterial and urinary bladder smooth muscle.

Human arterial blood vessels were obtained post-mortem and immediately immersed in cold physiological saline solution. Within 24 hours of removal the isolated arterial tissue was placed in Krebs' solution (comprising in mM concentrations: NaCl, 118.5; NaHCO$_3$, 25; dextrose, 5; KCl, 4.8; CaCl$_2$, 2.5; MgSO$_4$, 1.2; KH$_2$PO$_4$, 1.2; cocaine, 0.03; corticosterone, 0.03; propranolol, 0.001; ascorbic acid, 0.1; and indomethacin, 0.01). The arteries were dissected free from extraneous tissue and then cut into cross sectional rings approximately 3 mm in length. The arterial rings were suspended vertically in 10 mL tissue baths and bathed in Kreb's solution maintained at 37° C. and constantly aerated with a 95% O$_2$ and 5% CO$_2$ gas mixture. A resting tension of 1 to 1.5 g was applied to each ring and thereafter periodically readjusted to maintain a 1 g resting tension throughout the duration of the assay.

Human prostatic and bladder neck smooth muscle tissue was obtained following radical cystoprostatectomies or radical prostatectomies and immediately immersed in Krebs' solution. The prostatic and bladder tissue was dissected free from extraneous tissue and then strips of tissue 0.8 to 1.2 cm in length and 3 to 5 mm in width were cut and suspended vertically in 10 mL tissue baths and bathed in Kreb's solution maintained at 37° C. and constantly aerated with a 95% O$_2$ and 5% CO$_2$ gas mixture. A resting tension of 0.75 to 1 g was applied to each muscle strip and thereafter periodically readjusted to maintain a 1 g resting tension throughout the duration of the assay.

The arterial ring and prostatic and bladder neck strip preparations were allowed to equilibrate for 60 minutes during which period the bath solution was replaced every 15 minutes. The tissue was then exposed to bath solution containing norepinephrine (1 to 10 µM) and once a steady state contraction was produced the tissue was exposed to bath solution free of norepinephrine, replacing the solution twice every 5 minutes for 30 minutes. The arterial ring and prostatic and bladder neck strip preparations were exposed to norepinephrine in a cumulative concentration fashion. That is, the isolated tissue was exposed to bath solution containing a threshold concentration of norepinephrine until a steady state contractile response was a rained and then the concentration of norepinephrine was cumulatively increased by 0.5 log increments until a maximal or near maximal response was attained. Norepinephrine produced a concentration-dependent, $\alpha_1$-adrenoceptor mediated contraction of the arterial ring and of the prostatic and bladder neck strip preparations.

The tissue was then exposed to solution free of norepinephrine, replacing the solution twice every 5 minutes for 30 minutes. After baseline tension was established and readjusted to 1 g, the tissue was exposed to bath solution containing the test compound, replacing the solution every 15 minutes for 60 minutes. In the presence of the test compound, the tissue again was exposed to norepinephrine in a cumulative concentration fashion, increasing the norepinephrine concentration until a maximal or near maximal response was achieved.

The concentration ratio (CR) of norepinephrine necessary to produce equiactive responses in the absence and presence of the test compound was determined. Relying on the concentration ratio, the assay concentration (molar) of the test compound, and the relationship:

$$pA_2 = -\log \frac{[\text{test compound}]}{CR - 1}$$

the negative log of the dissociation constant ($pA_2$) for each test compound at $\alpha_1$-adrenoceptors were estimated for the arterial ring and prostatic and bladder neck strip preparations.

Proceeding as in Example 40, compounds of Formula I were tested and found to selectively inhibit the $\alpha_1$-adrenoceptor mediated contractions of human, isolated prostatic and bladder neck smooth muscle. In contrast, prazosin non-selectively inhibited the $\alpha_1$-adrenoceptor mediated contractions of both human, isolated prostatic/bladder neck smooth muscle and isolated arterial smooth muscle.

EXAMPLE 41

Rat In Vivo, Blood Pressure Assay

The following describes an in vivo assay for measuring the effect of test compounds on blood pressure in normotensive and spontaneously hypertensive rats.

Normotensive or spontaneously hypertensive rats (0.25 to 0.45 kg) were fasted for 18 hours and anesthetized with ether. The right femoral vein was isolated and cannulated with a fluid filled polyethylene cannulae for bolus administration of test substances. The right femoral artery was isolated and cannulated with a fluid filled polyethylene cannula connected to an external pressure transducer for monitoring mean arterial blood pressure (MAP).

The rats were placed in restrainers and allowed to recover from anesthesia. Following a 30 minute period for stabilization, test compounds or vehicle were administered, i.v., and blood pressure was monitored continuously for at least 4 hours post-administration.

Proceeding as in Example 41, compounds of Formula I were tested and found to be considerably less potent than prazosin at producing blood pressure lowering effects.

EXAMPLE 42

Rat In Vivo, Tilt-Response Assay

The following describes an in vivo assay in normotensive rats for measuring the propensity of test compounds to inhibit the reflex maintenance of basal blood pressure levels in response to vertical tilt.

Normotensive rats (0.25 to 0.45 kg) were fasted for 18 hours and anesthetized with ether. The right femoral vein was isolated and cannulated with a fluid filled polyethylene cannulae for bolus administration of test substances. The right femoral artery was isolated and cannulated with a fluid filled polyethylene cannula connected to an external pressure transducer for monitoring mean arterial blood pressure (MAP).

The rats were restrained in a supine position and allowed to recover from anesthesia. Following a 30 minute period for stabilization, test compounds or vehicle were administered, i.v., and blood pressure was monitored continuously while the rats were tilted vertically at 30 to 60 degrees from supine at 15, 30 and 45 minutes post-administration.

Proceeding as in Example 42, compounds of Formula I were tested and found to be considerably less potent than prazosin at inhibiting the reflex maintenance of basal blood pressure levels in response to vertical tilt.

EXAMPLE 43

Dog In Vivo, Blood and Intraurethral Pressure Assay

The following describes an in vivo assay for measuring the relative effect of test compounds on hypogastric nerve stimulation-induced increases in intraurethral pressure and phenylephrine-induced increases in diastolic blood pressure in anesthetized dog.

Mongrel dogs (10 to 20 kg) were fasted for 12 to 18 hours and anesthetized with pentobarbital sodium (35 mg/kg, i.v.). An endotracheal tube was inserted and thereafter the lungs were mechanically ventilated with room air. The right femoral vein was isolated and cannulated with two polyethylene cannulae, one for the administration of a continuous infusion of pentobarbital sodium (5 to 10 mg/kg/hr) and the other for bolus administration of test substances. The right femoral artery was isolated and cannulated to the abdominal aorta with a fluid filled polyethylene cannula connected to an external pressure transducer for monitoring diastolic aortic pressure (DAP). The bladder was exposed via a ventral midline abdominal incision and emptied of urine through a 22 gauge needle. The bladder was cannulated through a stab incision with a water filled balloon catheter connected to an external pressure transducer for monitoring prostatic intraurethral pressure (IUP). The right hypogastric nerve (HGN) was carefully isolated and attached to a Dastre's electrode for nerve stimulation.

The preparation was allowed to stabilize for a least 30 minutes and must have had a stable basal IUP for not less than 15 minutes prior to commencement of the assay protocol. The HGN was stimulated (20–50 V, 10 Hz, 10 msec pulse train for 10 sec) to induce a measurable increase in IUP and then phenylephrine (PE) was administered by bolus injection (0.5 to 0.6 µg/kg, i.v.) to induce a measurable increase in DUP. The HGN stimulation and PE bolus injection were repeated every 5 minutes until three consecutive reproducible increases in IUP and DAP were achieved. Vehicle (0.1 to 0.3 mL/kg) was administered and 20 minutes later the HGN stimulation and PE bolus injection were repeated. Test compound was then administered and 20 minutes later the HGN stimulation and PE bolus injection were repeated. Test compound was administered approximately every 20 minutes, increasing the dose until maximal or near maximal inhibition of the increases in IUP and DAP was attained.

Proceeding as in Example 43, compounds of Formula I were tested and found to selectively inhibit the HGN stimulation-induced increases in IUP. In contrast, prazosin inhibited increases in IUP and DAP in a similar fashion.

We claim:

1. A method for treating an obstructive uropathy treatable by administration of an $\alpha_1$-adrenoceptor antagonist in an animal in need of such treatment, which method comprises administering to such animal a therapeutically effective amount of a compound of the formula:

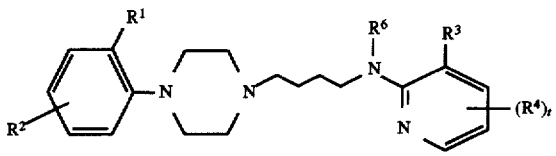

in which:

t is 0, 1 or 2;

$R^1$ is hydro, hydroxy, halo, nitro, amino, cyano, $(C_{1-4})$ alkylthio, acetylamino, trifluoroacetylamino, methylsulfonylamino, $(C_{1-6})$alkyl, $(C_{3-6})$cycloalkyl, $(C_{3-6})$cycloalkyl $(C_{1-4})$alkyl, oxazol-2-yl, aryl, aryl $(C_{1-4})$alkyl, $(C_{1-6})$alkyloxy, $(C_{3-6})$cycloalkyloxy, $(C_{3-6})$ cycloalkyl $(C_{1-4})$alkyloxy, 2-propynyloxy, aryloxy or aryl $(C_{1-4})$alkyloxy (wherein alkyl is optionally substituted with one to three halo atoms and aryl is optionally substituted with one to two substituents independently selected from halo and cyano);

$R^2$ is hydro, hydroxy, halo, cyano, $(C_{1-6})$alkyl or $(C_{1-6})$ alkyloxy (wherein alkyl is optionally substituted with one to three halo atoms);

$R^3$ is $—C(O)R^7$ (wherein $R^7$ is $(C_{1-6})$alkyl, $(C_{3-6})$ cycloalkyl, di$(C_{1-4})$alkylamino, N—$(C_{1-4})$alkyl-N—$(C_{1-4})$alkyloxyamino, pyrrolidin-1-yl, piperidin-1-yl, morpholin-4-yl or piperazin-1-yl);

$R^4$ is halo, hydroxy, cyano, $(C_{1-6})$alkyl or $(C_{1-6})$alkyloxy; and $R^6$ is hydro or $(C_{1-6})$alkyl);

or a pharmaceutically acceptable salt or N-oxide thereof.

2. The method of claim 1 in which t is 0 or 1; $R^1$ is methylthio, methylsulfonylamino, $(C_{1-4})$alkyl, cyclopropyl, oxazol-2-yl, $(C_{1-3})$alkyloxy or cyclopropylmethoxy (wherein alkyl is optionally substituted with three halo atoms); $R^2$ is hydro, fluoro or methyl; $R^3$ is dimethylaminocarbonyl or N-methyl-N-methoxyaminocarbonyl; when present $R^4$ is a substitution at the 5-position selected from halo, cyano or methyl; and $R^6$ is hydro.

3. The method of claim 2 in which t is 0 and $R^1$ is methylthio, n-propyl, cyclopropyl, oxazol-2-yl, methoxy, trifluoromethoxy, 2,2,2-trifluoroethoxy or cyclopropylmethoxy.

4. The method of claim 3 in which the compound is 2-{3-[4-(2-methoxyphenyl)piperazin-1-yl]-propylamino}-N,N-dimethylnicotinamide or a pharmaceutically acceptable salt thereof.

5. The method of claim 4 in which the compound is 2-{3-[4-(2-methoxyphenyl)-piperazin-1-yl]propylamino}-N,N-dimethylnicotinamide hydrochloride.

6. The method of claim 1 in which the obstructive uropathy is caused by benign prostatic hyperplasia.

7. The method of claim 6 in which t is 0 or 1; $R^1$ is methylthio, methylsulfonylamino, $(C_{1-4})$alkyl, cyclopropyl, oxazol-2-yl, $(C_{1-3})$alkyloxy or cyclopropylmethoxy (wherein alkyl is optionally substituted with three halo atoms); $R^2$ is hydro, fluoro or methyl; $R^3$ is dimethylaminocarbonyl or N-methyl-N-methoxyaminocarbonyl; when present $R^4$ is a substitution at the 5-position selected from halo, cyano or methyl, and $R^6$ is hydro.

8. The method of claim 7 in which t is 0 and $R^1$ is methylthio, n-propyl, cyclopropyl, oxazol-2-yl, methoxy, trifluoromethoxy, 2,2,2-trifluoroethoxy or cyclopropylmethoxy.

9. The method of claim 8 in which the compound is 2-{3-[4-(2-methoxyphenyl)piperazin-1-yl]-propylamino}-N,N-dimethylnicotinamide or a pharmaceutically acceptable salt thereof.

10. The method of claim 9 in which the compound is 2-{3-[4-(2-methoxyphenyl)-piperazin-1-yl]propylamino}-N,N-dimethylnicotinamide hydrochloride.

11. A compound selected from the group consisting of 2-(3-{4-[2-(2,2,2-trifluoroethoxy)phenyl]piperazin-1-yl}-propylamino)-N,N-dimethylnicotinamide, 2-(3-{4-[2-(2,2,2-trifluoroethoxy)phenyl]piperazin-1-yl}-propylamino-N-methyl-N-methoxynicotinamide, 2-{3-[4-(2-cyclopropylmethoxyphenyl)piperazin-1-yl]propylamino}-N,N-dimethylnicotinamide, 2-{3-[4-(2-oxazol-2-ylphenyl)piperazin-1-yl]propylamino}-N,N-dimethylnicotinamide, and the pharmaceutically acceptable salts thereof.

12. The compound of claim 11 which is 2-(3-{4-[2-(2,2,2-trifluoroethoxy)phenyl]piperazin-1-yl}-propylamino)-N,N-dimethylnicotinamide or a pharmaceutically acceptable salt thereof.

13. The compound of claim 12 which is 2-(3-{4-[2-(2,2,2-trifluoroethoxy)phenyl]piperazin-1-yl}-propylamino)-N,N-dimethylnicotinamide hydrochloride.

14. The compound of claim 11 which is 2-(3-{4-[2-(2,2,2-trifluoroethoxy)phenyl]piperazin-1-yl}-propylamino)-N-methyl-N-methoxynicotinamide or a pharmaceutically acceptable salt thereof.

15. The compound of claim 14 which is 2-(3-{4-[2-(2,2,2-trifluoroethoxy)phenyl]piperazin-1-yl}-propylamino)-N-methyl-N-methoxynicotinamide hydrochloride.

16. The compound of claim 11 which is 2-{3-[4-(2-cyclopropylmethoxyphenyl)piperazin-1-yl]propylamino}-N,N-dimethyl-nicotinamide or a pharmaceutically acceptable salt thereof.

17. The compound of claim 16 which is 2-{3-[4-(2-cyclopropylmethoxy-phenyl)piperazin-1-yl]propylamino}-N,N-dimethylnicotinamide oxalate.

18. The compound of claim 11 which is 2-{3-[4-(2-oxazol-2-ylphenyl)piperazin-1-yl]-propylamino}-N,N-dimethylnicotinamide or a pharmaceutically acceptable salt thereof.

19. The compound of claim 18 which is 2-{3-[4-(2-oxazol-2-ylphenyl)piperazin-1-yl]propylamino}-N,N-dimethylnicotinamide hydrochloride.

* * * * *